US009719962B2

(12) United States Patent
Sideris et al.

(10) Patent No.: US 9,719,962 B2
(45) Date of Patent: Aug. 1, 2017

(54) DEVICE AND METHOD FOR APPLYING A CONTINUOUS ELECTRIC FIELD

(75) Inventors: Dimitrios Sideris, Richmond (GB); Alex Iles, Teddington (GB); Richard Jackson, Teddington (GB)

(73) Assignee: Genetic Microdevices Limited, Teddington, Greater London (GB)

( * ) Notice: Subject to any disclaimer, the term of this patent is extended or adjusted under 35 U.S.C. 154(b) by 737 days.

(21) Appl. No.: 14/115,976

(22) PCT Filed: May 4, 2012

(86) PCT No.: PCT/GB2012/050973
§ 371 (c)(1),
(2), (4) Date: Dec. 11, 2013

(87) PCT Pub. No.: WO2012/153108
PCT Pub. Date: Nov. 15, 2012

(65) Prior Publication Data
US 2014/0083856 A1    Mar. 27, 2014

(30) Foreign Application Priority Data
May 6, 2011   (GB) .................................. 1107584.3

(51) Int. Cl.
G01N 27/447    (2006.01)
B01D 57/02     (2006.01)

(52) U.S. Cl.
CPC ....... G01N 27/44791 (2013.01); B01D 57/02 (2013.01); G01N 27/447 (2013.01);
(Continued)

(58) Field of Classification Search
CPC ............. G01N 27/447; G01N 27/4473; G01N 27/44713; G01N 27/44791
See application file for complete search history.

(56) References Cited

U.S. PATENT DOCUMENTS

| 4,911,817 A | 3/1990 | Kindlmann |
| 5,126,022 A * | 6/1992 | Soane ................... B01D 57/02 204/458 |

(Continued)

FOREIGN PATENT DOCUMENTS

| DE | 3931851 A1 * | 4/1991 | ............. G01N 27/26 |
| JP | H02165047 A | 6/1990 | |

(Continued)

OTHER PUBLICATIONS

EPO computer-generated English language translation of Heinrich et al. DE 3931851 A , patent published Apr. 11, 1991.*

(Continued)

Primary Examiner — Alexander Noguerola
(74) Attorney, Agent, or Firm — MacMillan, Sobanski & Todd, LLC

(57) ABSTRACT

A device comprises an electric field applying assembly adapted to generate an electric field having a discrete electric field profile; a conducting volume and an electrical interface region provided between the conducting volume and the electric field applying assembly such that the discrete electric field is applied to the material by the electric field applying assembly at a location spaced from the conducting volume, wherein the electrical interface region comprises at least an ionically conductive material arranged adjacent to an in contact with the conducting volume; such that the discrete electric field applied by the electric field applying assembly is smoothed by the electrical interface region so that the electric field profile established within the conducting volume is substantially continuous.

28 Claims, 19 Drawing Sheets

(52) U.S. Cl.
CPC . *G01N 27/44713* (2013.01); *G01N 27/44756* (2013.01); *Y10T 29/49002* (2015.01)

(56) References Cited

U.S. PATENT DOCUMENTS

| | | | |
|---|---|---|---|
| 5,302,264 A * | 4/1994 | Welch | G01N 27/44743 204/452 |
| 6,277,258 B1 | 8/2001 | Ivory et al. | |
| 7,294,247 B1 * | 11/2007 | Tian | G01N 27/44773 204/451 |
| 7,426,069 B2 | 9/2008 | Makii | |
| 8,035,763 B2 | 10/2011 | Im | |
| 8,262,884 B2 | 9/2012 | Sideris | |
| 2002/0070113 A1 | 6/2002 | Miles et al. | |
| 2007/0099200 A1 | 5/2007 | Chow et al. | |

FOREIGN PATENT DOCUMENTS

| | | |
|---|---|---|
| JP | 2000356622 A | 12/2000 |
| JP | 2004538482 A | 12/2004 |
| JP | 2005103423 A | 4/2005 |
| JP | 2005114433 A | 4/2005 |
| JP | 2007264153 A | 10/2007 |
| JP | 2008527320 A | 7/2008 |
| JP | 2009104137 A | 5/2009 |
| WO | 0171330 A1 | 9/2001 |
| WO | 03/015891 A1 | 2/2003 |
| WO | 03051520 A1 | 6/2003 |
| WO | 2006070176 A1 | 7/2006 |

OTHER PUBLICATIONS

Japanese Notification of Reasons for Rejection, Application No. 2014-508875 dated Apr. 5, 2016.
Erlandsson et al., "Electrolysis-reducing electrodes for electrokinetic devices," Electrophoresis, 2011, vol. 32, pp. 784-790.
Patents Act 1977: Search Report under Section 17(5), Application No. GB1107584.3, dated Aug. 25, 2011.
PCT International Search Report and Written Opinion, Application No. PCT/GB2012/050973, dated Jul. 26, 2012.

* cited by examiner

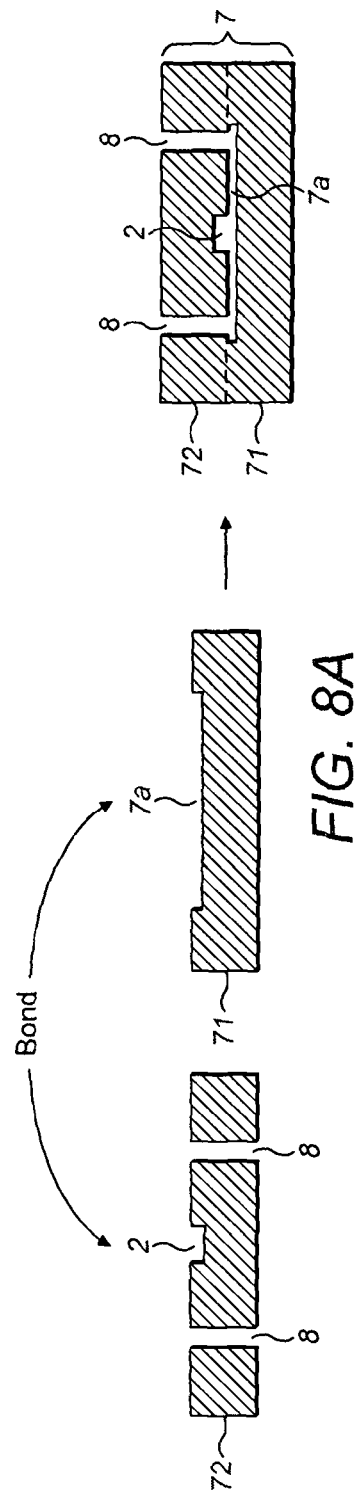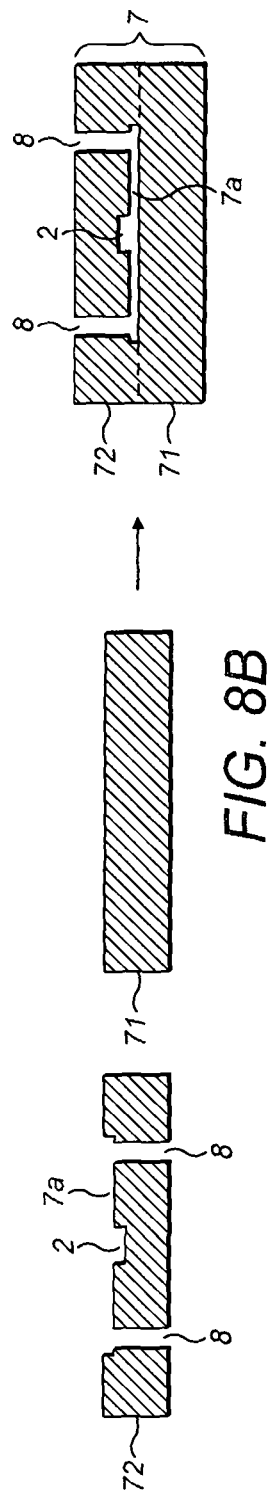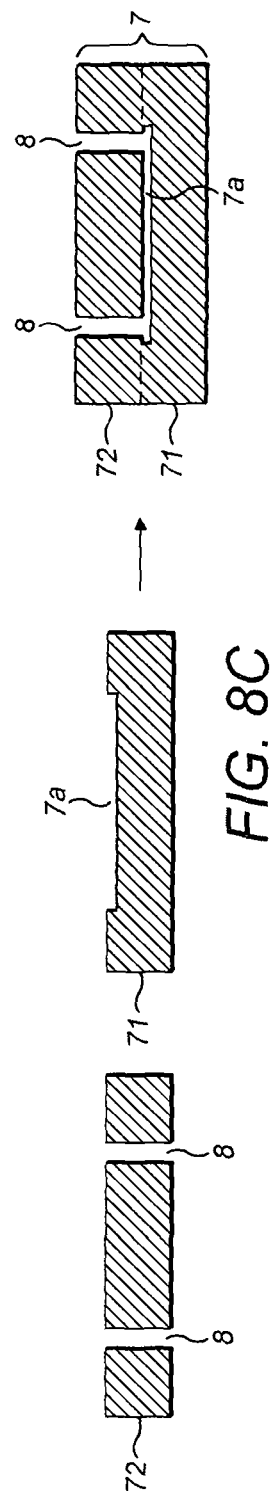

DEVICE AND METHOD FOR APPLYING A CONTINUOUS ELECTRIC FIELD

CROSS-REFERENCE TO RELATED APPLICATIONS

This application is the National Phase of International Application PCT/GB2012/050973 filed May 4, 2012, which designated the U.S. That International Application was published in English under PCT Article 21(2) on Nov. 15, 2012 as International Publication Number WO 2012/153108A1. PCT/GB2012/050973 claims priority to U.K. Application No. 1107584.3 filed May 6, 2011. Thus, the subject nonprovisional application also claims priority to U.K. Application No. 1107584.3 filed May 6, 2011. The disclosures of both applications are incorporated herein by reference.

BACKGROUND OF THE INVENTION

This invention relates to a device and method for applying an electric field, and methods of manufacture thereof. The invention is particularly suited for smoothing the shape of electric fields applied to microfluidic devices or "lab-on-chip" type devices ("LOCs").

Microfluidic devices such as LOCs have widespread applications. An increasing number of such applications relate to the sequencing and sorting of objects such as biomolecules, and the sorting of cells. Conventionally, the sequencing and sorting of biomolecules, and the sorting of cells, is carried out using electrophoresis. Electrophoresis techniques are well known and are often used to separate objects (sometimes referred to as 'analytes') according to their electrical and hydrodynamic properties. Other separation techniques include the use of centrifugal spectrometers as described in EP1455949.

In conventional electrophoresis, a constant and uniform electric field is applied to move objects through a fluid or another sieving matrix. As they move through this material, the objects experience forces which depend on their shape and size (e.g. hydrodynamic forces) and/or on their affinity for the material (e.g. chemical attraction/repulsion forces), and an electric force due to the applied field, which depends on their charge. As a result of the different forces experienced by each object type, the objects move with different terminal velocities depending on their individual characteristics and thus they separate into "bands".

In recent years, the concept of field shifting analysis for separation of objects has been proposed by one of the present inventors, wherein, rather than being constant, the applied electric field has a time dependent field gradient. Examples of electrophoresis devices which use this concept are described in WO 2006/070176, the entire content of which is hereby incorporated by reference. In comparison to conventional techniques, field shifting analysis offers enormous potential in terms of analytical and processing capabilities, offering several orders of magnitude faster and more sensitive separations.

Field shifting devices usually employ a network of electrodes to apply a suitable time dependent electric field gradient for the separation and manipulation of analytes and other materials in a microfluidic environment. For example, the microfluidic environment may involve a planar separation channel in or on a glass device, with cross sectional dimensions of the order of 0.1 to several hundred micrometers and a length of at least 500 μm.

Further examples of different electrophoresis devices can be found in U.S. Pat. No. 6,277,258 and US-A-2002/0070113.

In known microfluidic devices, including field shifting devices, the electric field is usually applied directly to the channel, via internal electrodes. This arrangement facilitates the generation of high electric fields by generating an electric current in a conducting separation buffer inside the channel. However, this configuration often leads to significant distortions to the electric field shape at the locus of each electrode along the channel. Accordingly, the field in the channel does not follow a smooth transition from high to low, as is desirable when implementing the field shifting technique for example, but instead consists of a series of steps. The separating molecules pass at very close proximity (contact) to the electrodes, "feeling" the field distortions and thereby degrading the resolution of separation. Similar problems are also encountered in other applications where it is desired to apply a shaped (i.e. non-uniform) electric field to a channel.

To address this problem, it has been proposed to increase the number of electrodes periodically positioned along the channel. However, in practice, such configuration does not completely reduce the electric field distortions for two reasons. The first reason is that it is impossible to position an infinite number of independently addressable electrodes along the channel. The second reason is that, since the electrodes have finite sizes, the voltage in the space immediately adjacent to the electrodes is constant (at a value approximately equal to the voltage of the electrode). Accordingly, the resulting electric field is zero. This can cause significant distortion in the overall electric field.

Another problem with conventional separation techniques, including known field shifting techniques, is that some analytes can be lost as rather than travelling past the electrodes as intended, the objects may travel towards the electrodes directly contacting the channel and effectively be removed from the separation process. Furthermore, gasses produced by electrolysis due to contact between the electrodes and the (typically aqueous) fluid in the channel enter the channel where they disrupt the electric field and the analysis.

Accordingly, there is a need for a technique which addresses the above issues.

SUMMARY OF THE INVENTION

In accordance with a first aspect of the present invention, a device comprises:
  an electric field applying assembly adapted to generate an electric field having a discrete electric field profile;
  a conducting volume; and
  an electrical interface region, provided between the conducting volume and the electric field applying assembly, the electrical interface region arranged such that the discrete electric field is applied to the electrical interface region by the electric field applying assembly at a location spaced from the conducting volume;
  wherein the electrical interface region comprises at least an ionically conductive material arranged adjacent to and in contact with the conducting volume;
  such that the discrete electric field applied by the electric field applying assembly is smoothed by the electrical interface region so that the electric field profile established within the conducting volume is substantially continuous.

In accordance with a second aspect of the present invention, a method for applying an electric field to a conducting volume, comprises the steps of:

provided an electric field applying assembly adapted to generate an electric field having a discrete electric field profile;

providing a conducting volume;

providing an electrical interface region between the conducting volume and the electric field applying assembly, wherein the electrical interface region comprises at least an ionically conductive material arranged adjacent to and in contact with the conductive volume; and applying the discrete electric field to the electrical interface region at a location spaced from the conducting volume;

such that the applied discrete electric field is smoothed by the electrical interface region so that the electric field profile established within the conducting volume is substantially continuous.

It will be appreciated that the term "conducting volume" is used here to describe any conductor which has a volume and in which a substantially continuous electric field is desired, at least in parts of the conducting volume. It will be understood that the nature of the conducting volume may vary depending on the type of application of the present invention. For example, the conducting volume may be a channel, such as a separation channel used in electrophoresis or other separation devices, or could comprise a plurality of such channels. In other applications, the conducting volume may represent a region such as a hydrophilic region provided in a hydrophobic paper substrate or a porous region provided in a porous hydrophobic substrate. In general, the conducting volume may represent any volume in which fluids or objects of interest may be accommodated (and/or may move through) during analysis, whether being physically constrained by a channel or other physical entity or not. For example, where the conducting volume comprises one or more channels, each one may or may not be physically delimited: the conducting volume could for instance encompass one or more paths (which may be thought of as 'imaginary' or 'virtual' channels) taken by analytes in 'free flow' electrophoresis devices or "slab-gel" techniques. The embodiments described below refer primarily to conducting volumes in the form of physically-defined channels for separation of objects, although it will be understood that this is not intended to be limiting.

The present invention therefore allows for smoothing of the applied electric field by converting the discrete electric field obtained from the electric field applying assembly (e.g. an electrode array) into a substantially continuous field in the conducting volume. A 'discrete' electric field is one with a field profile which is non-continuous, e.g. including gaps or sudden jumps or drops in magnitude, such as may be observed in a "step-profile" shaped field. For example, a discrete electric field may arise from multiple point voltage sources, each spaced from the next along the periphery of the conducting volume (e.g. in the case of a channel, along its path). By a 'substantially continuous' electric field it is meant an electric field which is smoother than the discrete electric field. For instance, in the above example, the value of the smoothed electric field preferably changes gradually in the interval between the location of one point voltage source and the next, from a value corresponding to that established by the first point source to a value corresponding to that established by the second. More generally, the substantially continuous field may be smoothly interpolated between the applied discrete values. However, depending on the degree of smoothing applied, the continuous field may depart to an extent from a perfect linear gradient or curve and could still include some discontinuities (albeit smaller in magnitude than those of the discrete field).

The field shaping is achieved by providing an electric interface region between the conducting volume and the electric field applying assembly which has suitable electrical and geometrical properties, whereby the electric field applying assembly is spaced away from the conducting volume by the electrical interface region. In particular, the field smoothing is performed, at least in part, by means of ionic current transport within an ionically conductive material forming part (or all) of the electrical interface region and arranged adjacent to and in contact with the conducting volume. This arrangement has the substantial advantage that any electrolysis takes place either within the electric interface region or at the electrodes (or other voltage source) and not in the conducting volume. In this way, there is no disruption to the environment within the conducting volume itself.

It should be noted that the electrical interface region does not need to be provided along the whole periphery of the conducting volume, but could extend along a portion of the conducting volume only. For example, where the conducting volume is a channel, the electrical interface region does not need to be provided along the whole length of the channel, but could extend along a portion of the channel only.

By 'adjacent to and in contact with' the conducting volume it is meant that the ionically conductive material is provided in direct electrical contact with the conducting volume, without any other material type inbetween. The electrical interface region can be made up of a single component (the ionically conductive material), or more than one component arranged in series (and in electrical contact with one another) between the electrical field applying assembly and the conducting volume. In one example, as will be described in more detail below, the electrical interface region may comprise an ionically conductive material adjacent to the conducting volume and a non-ionically conductive material, for instance an electrically resistive material, the non-ionically conductive material being provided between the electric field applying assembly and the ionically conductive material. However, in other advantageous embodiments, the electrical interface region consists of ionically conductive material. In other words, the electrical interface region is formed wholly of ionically conductive material. For instance, the aforementioned (single) ionically conductive material directly contacting the conducting volume may extend continuously between the conducting volume and the electrical field applying assembly. Alternatively, more than one ionically conducting component, or a mixture of ionically and non-ionically conducting components may be deployed in series between the conducting volume and the electrical field applying assembly to form the electrical interface region.

The term 'ionically conductive' means that the material conducts electricity by movement of ions. There may or may not also be movement of electrons or holes through the material. In addition to the portion of the electrical interface region contacting the conducting volume, the conducting volume is preferably also ionically conducting and not primarily electrically conducting. For example, the conducting volume may be a channel filled with an ionic conductor such an aqueous buffer, as will be described in more detail below.

It is desirable that the conductivity/resistivity of the one or more components making up the electrical interface region (and particularly that of the ionically conductive material)

should be configured to "match" that of the conducting volume. By "matched", it is not required that the or each component of the electrical interface region should have equal or at least similar ionic conductivity as that of the conductive volume, although this is preferred. What is necessary is that the relative conductivities/resistivities are balanced to avoid the electrical current being conducted preferentially by either the electrical interface region or by the conducting volume. If the conductivity of the electrical interface region is too high or too low, the field shape may not form as desired in the conducting volume. This is because, if the relative conductivities of the fluid and the ionically conductive material were markedly different, then, in accordance with Ohm's law, all the current arising from the applied voltages could pass only through the electrical interface region or only through the conducting volume. This would significantly alter the field smoothing effect, leading to over-smoothing or under-smoothing of the field. In particular, if the relative conductivity of the electrical interface region is too low, the electric field obtained in the conducting volume may be damped, i.e. appear much lower than the intended field applied at the electrodes, because the power is essentially lost in the electrical interface region.

To achieve matching, it is not essential that the resistivities/conductivities of the component(s) forming the electrical interface region and of the conducting volume are identical and indeed this is extremely difficult to achieve. However, in preferred configurations, the conductivities/resistivities are of the same order of magnitude. In particularly preferred embodiments, the ratio of the resistivities/conductivities of the component(s) making up the electrical interface region to that of the conducting volume (or vice versa) is between 1:100 and 1:1, preferably between 1:50 and 1:1, more preferably between 1:10 and 1:1.

Advantageously, the ionically conductive material contacting the conducting volume is impervious to gases (produced, for example by electrolysis at the electrodes) thereby preventing them from reaching the conducting volume. Alternatively, the geometry can be arranged to guide any gas bubbles away from the conducting volume. The ionically conductive material preferably prevents any analytes to be separated inside the conducting volume from reaching the electrodes. For example, any pores in the material are preferably too small to permit passage of the objects therethrough. This helps to retain the objects within the conducting volume and avoids sample loss.

In certain preferred examples, the electrical interface region has a thin, 'membrane'-like or 'film'-like geometry whereby its width (i.e. the distance between the electric field applying assembly and the conducting volume) is at least greater than its thickness in a direction perpendicular to both said distance and the conducting volume (e.g. the long axis of a channel). More preferably, the distance between the conducting volume and the electric field applying assembly is at least twice the thickness of the electrical interface region, more preferably at least 5 times the thickness of the electrical interface region, further preferably at least 5 times, still preferably at least 10 times, most preferably at least 100 times.

The preferred membrane-like geometry effectively averages out the voltages obtained between the electrodes. This 'spreads out' each point voltage along the periphery of the conducting volume (with relatively little voltage dispersion in any other direction), thereby enabling smoothing of the discrete applied field from the electric field applying assembly primarily along the periphery of the conducting volume. By keeping the material thin, the voltage can be arranged to be substantially constant in the material's thickness direction, avoiding the establishment of transverse electric fields in the conducting volume. However, this can alternatively be achieved by arranging the electric field applying assembly to apply a discrete electric field which does not vary in the thickness direction of the electrical interface region (e.g. by the use of electrodes which contact the material across its full thickness).

Alongside the smoothing of the electric field, at the same time the electrical interface region keeps the microfluidic environment inside the conducting volume separate from the electrodes so as not to disrupt the separation or manipulation process.

Preferably, the conducting volume is provided in or on a substrate and the electric interface region substantially fills a cavity in or on the substrate. The substrate itself can be conveniently fabricated using selected microfabrication techniques.

Preferably, the depth of the conducting volume is approximately equal to or greater than the thickness of the interface region in the same direction. In particular, the depth of the conducting volume is preferably between 1 and 5 times greater, preferably between 1.5 and 3 times greater, still preferably around 2 times greater than the thickness of the material. The inventors have found that this proportion enables formation of a conducting volume in the form of a channel by means of capillary forces acting on the electrical interface region material in fluid form, as will be described below.

In preferred embodiments, the distance between the location at which the discrete electric field is applied and the conducting volume is between 0.1 and 8 mm, preferably between 0.5 and 2.5 mm. Preferably, the thickness of the electrical interface region is between 0.1 and 100 µm, preferably between 20 and 40 µm. Preferably, the depth (height) of the conducting volume is between 0.1 to 500 µm, preferably between 10 and 100 µm.

In certain circumstances, it is desirable that the cavity in the substrate be provided with at least one pillar to provide support and prevent collapse of the top piece of the substrate. Pillars may also be deployed to alter the electrical properties of the interface, as mentioned below. Furthermore, pillars provide additional surface area to help retain the material(s) in the electrical interface region.

In preferred embodiments, the conducting volume is a channel which can follow any desirable path. For example, the channel may be rectilinear or may be in the form of a closed loop. The closed loop configuration provides several advantages over open loop designs such as a rectilinear channel. Firstly, closed loop channels avoid edge effects whereby the electric field obtained inside the channel at either end of the channel, deviate from the desired levels. For example, in a linear channel, a section in the middle of the channel will typically be presented with applied voltage sources either side of the section along the channel, the voltage obtained in the section being an average of the two voltages. A section near an end of the channel, however, does not "see" voltage sources provided on both sides, but only on the side towards the other end of the channel. This means that there is an asymmetric averaging, which causes a distortion in the field inside the section near the end of the channel. Secondly, when applying time-shifting electric fields to open loop channels, regions may occur where the field varies very little and the electric current direction remains essentially unchanged. This can lead to severe localised ion depletion in the ionically conductive material comprised in the electrical interface region. As a result, the desired field shape in the channel is lost since the effects of ion depletion tend to counteract the applied field. In contrast, in a closed loop channel, such as a circular arrangement, a propagating electrical "wave" (i.e. a shaped, non-uniform electric field profile) can be configured to travel around the loop. This 'sweeps' ions in the ionically conductive material around the loop, continuously replenishing any ion denuded regions and carries away ions from correspondingly over concentrated areas, so that the field in the channel remains smooth and stable. Thirdly, when an open loop channel is utilised, the effective operational length of the device is dictated by the physical length of the channel. In closed loop systems, there is no beginning or end to the main channel and so the device has essentially an infinite operational length.

Preferably, the electric field applying assembly comprises a plurality of electrodes in electrical contact with the electrical interface region and the electric field applying assembly further comprises a controller adapted to apply a voltage to each electrode in order to obtain a desired field profile.

The electrodes are preferably spaced from one another along a direction conforming to a periphery of the conducting volume. For example, where the conducting volume is a channel, it is preferable that the electrodes are spaced along a direction conforming to the path of the channel.

In preferred embodiments, the plurality of electrodes is arranged along one side of the conducting volume. Advantageously, the electric field applying assembly may further comprise a second plurality of electrodes arranged along the opposite side of the conducting volume from the first plurality of electrodes, thereby forming pairs of electrodes on opposite sides of the conducting volume and wherein a voltage can be applied to each electrode of the pair. In some preferred embodiments, substantially the same voltage is applied to both electrodes in each pair. However in other cases different voltages may be applied to each electrode in the pair, e.g. in order to counteract differential velocity effects due to curvature of the conducting volume (as described in WO2006/070176), or to laterally manipulate the field within the volume.

The device may further comprise an electric field measuring assembly adapted to measure the electric field in the conducting volume, (and/or along the electrical interface material); and wherein the controller is advantageously adapted to vary the applied discrete electric field based on the measured electric field. Accordingly, apart from 'write' electrodes applying the discrete electric field, 'read' electrodes may be used for measuring and controlling the applied field. The 'read' electrodes may contact the conducting volume directly or may measure the established electric field via a portion of electrical interface region (which may or may not be the electrical interface region located between the conducting volume and the electric field applying assembly). For example, the electric field measuring assembly may preferably comprise a plurality of electrodes in electrical contact with the electrical interface region, the plurality of electrodes of the electric field measuring assembly preferably being arranged on the opposite side of the conducting volume from the electric field applying assembly. In alternative advantageous embodiments, the device may use the same electrode(s) as write or read electrode(s), switching between the two modes as required. For example, the controller could be adapted to stop supplying voltage to each electrode for a short period at regular intervals, and to instead read the local field instantaneously, before resuming voltage supply.

The substrate can be provided with holes (also referred to as wells or well nodes) in connection with the cavity (and the interface region filling the cavity) and with a surface of the substrate, for accommodating an electrode in use. The holes can be filled with ionically conducting fluid, such as an aqueous buffer, a thixtropic gel or a viscous gel, and arranged such that electrodes are dipped in the ionically conducting fluid. Advantageously, this configuration provides escape points for the gas products of electrolysis. Furthermore, providing the substrate with holes filled with an ionic conductor allows for a sufficient ion reservoir size to mitigate ion depletion in the ionically conductive material comprised in the electrical interface region. As an alternative to dipped electrodes such as those described above, conducting electrodes (e.g. formed of a metal film) may be deposited on the substrate, leading to one or more connector(s) on the device for integrating with an electric field control system. These electrodes would be in contact with the interface material and vents could be provided for the escape of electrolysis gases.

Advantageously, the electric field applying assembly further comprises connecting arms, such as fluidic arms arranged to electrically connect each electrode to the electrical interface region. For example, the above-mentioned wells can be connected to a cavity filled with the electrical interface region via such connection arms. The use of fluidic arms in the electric field applying assembly provides increased design flexibility. For instance, the holes may be drilled in a top piece of the substrate and have any configuration as found convenient for the application, while the fluidic arms act as conductors for applying the voltages to the electrical interface region. By careful design of each arm's dimensions (and hence the electrical resistance it presents), the voltage level presented to the material can be controlled. Each connection arm preferably connects a single one of the electrodes to the electrical interface region.

Where the conducting volume is a channel, the holes in the substrate may be periodically spaced along a single line which follows the periphery of the conducting volume. However, this is not essential and each hole could be positioned at a different distance from the conducting volume. In one example, the holes may be staggered with respect to the periphery of the conducting volume in order to maximise the number of holes that can be provided along the periphery of the conducting volume. The different positions of the holes (and, hence, the electrodes they contain in use) could be negated by design of fluidic arms of the electric field applying assembly between the hole and the material. However, in other examples, the varying distances could be made use of in the establishment of the voltage variation required to create an electric field along the periphery of the conducting volume.

If the conducting volume is in the form of an open loop (e.g. a channel having at least two distinct "ends"—whether defined physically or not), the electric field applying assembly may be configured to counter field edge effects. For example, in the case of a linear channel, two additional electrodes may be arranged to provide an extra voltage at each end of the channel. Preferably, these electrodes are inserted in well nodes on the channel, wherein the well nodes can also serve as inlets and/or outlets for the channel.

As mentioned above, the electrical interface region may comprise more than one component and in one preferred embodiment comprises a non-ionically conductive material in addition to the ionically conductive material, such that the ionically conductive material is located between the non-ionically conductive material and the conducting volume and the discrete electric field is applied by the electric field applying assembly to the non-ionically conductive material. For example, the non-ionically conductive material can be placed between the ionically conductive material and the electrodes. The non-ionically conductive material conducts primarily by means of electron (and/or hole) movement and may be, for example, a resistive polymer or a semiconductor such as silicon.

In such embodiments, preferably, the conductivity/resistivity of the non-ionically conductive material and the conductivity/resistivity of the ionically conductive material are matched. As described above in relation to the relative conductivities/resistivities of the conducting volume and electrical interface region, in the present context the term "matched" does not mean that the conductivities/resistivities have to be equal, although it is preferred that they are at least similar. By "matching" the conductivities/resistivities of the two (or more) components of the electrical interface region, both conductivities/resistivities are taken into account along with the applied field parameters such that both the non-ionically conductive material and the ionically conductive material contribute to the smoothing of the discrete electric field. If, on the other hand, the relative conductivities of the two materials were markedly different, then in accordance with Ohm's law, all the current arising from the applied voltages could pass only through the ionically conductive material or only through the non-ionically conductive material. This would significantly alter the field smoothing effect, leading to over-smoothing or under-smoothing of the field and possibly field-shielding effects. Therefore, in preferred configurations, the conductivities/resistivities of the components are of the same order of magnitude. In particularly preferred embodiments, the ratio of the two materials' resistivities/conductivities is between 1:100 and 1:1, preferably between 1:50 and 1:1, more preferably between 1:10 and 1:1.

The same considerations apply to an electrical interface region comprising two or more ionically conductive components in series, or a mixture of ionically and non-ionically conductive components, in which case the conductivities/resistivities of each component are preferably "matched".

Configurations including a non-ionically conductive material as part of the electrical interface region provide several advantages. In particular, they provide flexibility in the connectivity with the electric field applying assembly. For example, electrodes may be connected to a "dry" solid material (e.g. silicon) instead of being dipped in fluid-filled wells as described above. This can result in a more coherent and sealed device. On the other hand, a disadvantage of such configurations is that the combination of an ionically conductive material (typically containing fluid) and a "dry", non-ionically conductive material requires a fluid/solid interface which tends to give rise to electrolysis and evolution of gas bubbles. Accordingly, such configurations may require pores or wells located at this interface to act as exhausts for the gas bubbles.

The ionically conductive material may comprise for example a polymer. Advantageously, polymers may be easily introduced into a device according to the invention in liquid form and then polymerised in situ, either using a chemical initiator, or by thermal or photo-initiation, for example.

Preferably, the ionically conductive material is a porous material. A 'porous' material is one through which fluid can flow, for example though pores, channels or cavities of the material. A foam, a sponge or any other type of matrix-like or cellular material, are examples of porous materials. For example, the ionically conductive, porous material, may comprise a porous glass or a porous ceramic material.

Alternatively, the ionically conductive material may be a hydrogel. Hydrogels are a class of polymeric materials that are able to absorb aqueous solutions but do not dissolve in water. Hydrogels have many attributes which make them highly suitable for use in the presently-disclosed field shaping interface. In particular, they are porous, typically having pore sizes in the low nm range, which means that they are permeable to water molecules and small ions, but impervious to large analytes, including biomolecules such as proteins or DNA. Furthermore, hydrogels are typically impervious to gas bubbles, thereby preventing the gases formed by electrolysis at the electrodes from reaching the conducting volume.

In a preferred embodiment, the resistivity of the electrical interface region is constant throughout its volume. Electrical homogeneity of the electrical interface region is generally desirable so as to achieve an isotropic field smoothing effect. Alternatively, in other embodiments, the resistivity may vary in at least one direction—for example, in a direction perpendicular to the periphery of the conductive volume or the elongate direction of a channel. This could enable, for example, the application of different magnitude fields to a plurality of concentric circular channels each spaced by a portion of electric field interface region, whilst using a single electric field applying assembly.

Varying the resistivity of the electrical interface region can be achieved by altering the composition of the region material in one or more directions, e.g. through the use of multiple electrical interface components of different electrical properties. However, such alteration can be difficult in practice. Alternatively, the resistivity may be more easily varied by introducing pillars in the cavity and varying either their size or their density in one or more directions. This has the effect of removing conducting material and thus increasing the resistivity of the electrical interface region (or reducing it if the density of the pillars drops). Another example method for varying the resistivity of the electrical interface region is to vary the depth of the cavity.

The conductivity and relative thickness of the electrical interface region is preferably such that current flow is not excessive, in order to avoid Joule heating and excessive electrolysis at the regions where electrodes are applied.

In preferred embodiments, the substrate is electrically resistive or insulating. It may be desirable that the substrate is transparent to any one or more of: visible, infrared (IR) or ultraviolet (UV) radiation to allow for photo-patterning and photo-polymerisation of the electrical interface region material through the substrate, or to make the device suitable for use with optical detection techniques. However, in other cases the substrate need not be optically transparent.

Advantageously, a device according to the invention may allow for simultaneous analysis in the conducting volume. For example, the volume may comprise a plurality of channels, each laterally spaced from the next by a region of electrical interface region, wherein the electric field applying assembly is configured to apply the discrete electric field to one portion of the electrical interface material, whereby the discrete electric field is smoothed by the electrical interface region such that a substantially continuous electric field is established in each of the plurality of channels. In a preferred configuration, the substantially continuous electric field established in each channel is substantially the same, although, as noted above, this is not essential. As an alternative, multiple channels could be stacked one on top of the other within the conducting volume, each layer containing a channel separated by a layer of insulator, with the electrical interface material in contact with one or both sides of each of the channel layers. In another example, interface material layers and conducting volume (channel) layers could be stacked one on top of the other, separated by insulating layers. Inlet channels for the introduction of samples to the separation channels within the conducting volume could be embedded in the insulating layers.

A device in accordance to the invention may be, for example, a microfluidic device and/or a separation device for separating objects, wherein the conducting volume is a separation channel. For example, the device may be a separation device for separating objects, the separation device comprising: a device according to the present invention, wherein the conducting volume is a separation channel which, in use, contains objects to be separated, whereby the substantially continuous electric field in the channel gives rise to an electric force acting on each object; and a balancing source configured to give rise to a force opposing the electric force on each object; whereby objects in the separation channel are caused to separate into bands under the combined influence of the electric field and the balancing source. The "balancing" force or forces arising from the balancing source may simply be force(s) due to the hydrodynamic resistance of an object passing through a static fluid or gel, or the conducting volume may be filled with a chromatographic column or micelles, so that the balancing force(s) may arise as a result of size exclusion and/or affinity chromatographic processes. The balancing force could also result from the hydrodynamic or electro-osmotic pumping of fluid through the conducting volume.

In a preferred embodiment, the device is an electrophoresis device, wherein the balancing source is a fluid contained in the channel together with the objects to be separated, the device further comprising a controller adapted to vary the applied discrete electric field so as to adjust the electric field profile relative to the separation channel, whereby objects in the separation channel are caused to separate into bands under the combined influences of an electric force due to the electric field established within the channel and a hydrodynamic force due to the fluid. Thus, in this case the balancing force is a hydrodynamic force.

In accordance with a third aspect of the present invention, a method of manufacturing a device comprises the steps of:
   providing an electric field applying assembly adapted to generate an electric field having a discrete electric field profile;
   providing a conducting volume;
   providing an electric interface region, between the conducting volume and the electric field applying assembly, wherein the electrical interface region comprises at least an ionically conductive material arranged adjacently to and in contact with the conducting volume, whereby, in use, the discrete electric field is applied to the electrical interface region at a location spaced from the conducting volume;
   such that, in use, the applied discrete electric field is smoothed by the electrical interface region so that the electric field profile established within the conducting volume is substantially continuous.

Advantageously, the conducting volume may be etched into the surface of a substrate using selected micromachining techniques. Alternatively, the conducting volume may be provided by mounting together two or more plates, at least one of which is etched or otherwise machined, to form a substrate containing a conducting volume (e.g. an internal channel).

Advantageously, a cavity may be formed in the substrate, using similar micromachining techniques. The cavity may then be filled with a prepolymer such as a monomer or material in liquid form, e.g. a liquid prepolymer which may be subsequently polymerised or cured to form at least one component of the electrical interface region. Typically, this is the ionically conductive component of the electrical interface region. Preferably, the material is hydrated prior to insertion/injection into the cavity (and prior to curing/polymerisation). This reduces the possibility of the material changing substantially in volume (particularly, swelling) once inside the cavity which may occur if the material were hydrated after curing. This could lead to cracking of the substrate and/or reduction in volume of the conducting volume.

In preferred embodiments, the polymerisation is achieved using a photo-initiator or a thermal-initiator. A photo-initiator is a catalyst ingredient that makes a polymer sensitive to light, typically UV irradiation. The polymerisation process is driven by free radicals which are produced by the photo-initiator upon exposure to radiation of the appropriate wavelength. Photo-initiators usually produce free radicals when exposed to photons, typically UV, but could also be activated by visible light or even an electron beam. Thus polymerisation of the material can be controlled by irradiation with, for example, UV light. It is also possible to use a suitable initiator that does not require thermal or photo initiated means to polymerise the material of the electrical interface region. One example is the APS/TEMED initiation of acrylamide.

This leads to the possibility of photo-patterning the material to define the channel therein. For example, a mask may be placed over the region of the device where the conducting volume is to be formed. Upon exposure to photo-initiating radiation, the unmasked regions of the material are cured whilst the masked conducting volume remains fluid. The material within the conducting volume can then be removed, e.g., by flushing, to form the desired volume. In particularly preferred examples, the flushing step can take place using a fluid which the conducting volume is to contain in use, e.g. a buffer or sieving gel, whereby the conducting volume is immediately primed for use.

Similarly, a thermal-initiator can be used to control polymerisation by increasing temperature. Thermal initiators are molecules that break down when heated, forming free radicals. Heating could be global (e.g. heating of the entire device) or localised, for example by using microwave radiation or lasers. Thus similar patterning of the electrical interface region can be achieved. Following polymerisation of the electrical interface material, the device may be soaked in buffer to allow its ionic content to equilibrate before the device is used.

Alternatively, the conducting volume may be obtained by utilising capillary forces acting on the electrical interface region material in liquid form, e.g. on the prepolymer before its polymerisation. The conducting volume (e.g. a channel) may be obtained using a cavity of suitable dimensions, wherein the depth of the channel is greater than the thickness of the interface region, preferably around twice the thickness of the interface region. This has been found by the present inventors to enable filling of the cavity whilst preventing filling of the channel. However, as mentioned above, other dimensions of the cavity/channel may also be able to achieve this effect, depending on the viscosity of the fluid interface region material and the surface energy of the particular material from which the substrate is made (amongst other parameters). For example, the depth of the channel is preferably between 1 and 5 times greater, preferably between 1.5 and 3 times greater, than the thickness of the cavity. Once the cavity is suitably filled with the prepolymer, the prepolymer can be polymerised as described above.

Prior to filling the cavity with the prepolymer, the cavity surfaces may be treated, for example by silanisation, in order to enhance the adhesion of the electrical interface region material to the substrate. It is also possible to pattern the material by selective silanisation of different areas of the cavity, making some areas hydrophobic and some areas hydrophilic. A silanising agent could alternatively or additionally be added to the prepolymer mixture if desired.

In another example, a physical stop could be formed between the cavity and the conducting volume to prevent the material entering the conducting volume. For example, a region of reduced dimension may be sufficient to halt the advance of the fluid material.

Preferably, the conducting volume is treated in a suitable way so that, during analysis of objects or analytes of interest present inside the conducting volume, they are prevented from sticking to the inner walls or inner surface of the conducting volume. For example, the inner surface of the conducting volume may be silanised or coated with a suitable material such as a polymer.

BRIEF DESCRIPTION OF THE DRAWINGS

Examples of devices and methods for smoothing the shape of an electric field as well as methods of manufacturing the device in accordance with the present invention will now be described with reference to the following Figures:—

FIGS. 8A to 8C depict further exemplary methods of manufacturing devices in accordance with the present invention;

DETAILED DESCRIPTION OF THE PREFERRED EMBODIMENTS

It will be appreciated that the devices and methods in accordance with the exemplary embodiments described herein have widespread applications, and may be used in any device which requires the application of a smooth electric field, such as microfluidic devices or LOCs for example. Potential applications include electrophoresis-like techniques, used for separation of objects, or other separation techniques such as centrifugal spectrometry as described in EP1455949. Alternative applications include microfluidic devices for separating objects in hydrophilic regions provided for example in hydrophobic paper substrates, in 'freeflow' electrophoresis devices, in slab-gels, or in electrochromatography.

The exemplary embodiments described below will focus on electrophoresis applications for separating objects in channels, particularly electric field shifting techniques of the type described in WO 2006/070176, but it will be understood that this is not intended to be limiting.

The 'objects' to be separated may comprise for example polymers such as proteins, DNA molecules, RNA molecules or other types of biomolecules such as biological cells. Inorganic objects such as particulates, e.g. pigments, dyes, dust particles etc are also envisaged. At least some of the objects have an effective electrical charge such that they experience a force in the presence of an applied electric field. The charge may be intrinsic to the object (e.g. in the case of an ion), or may come about as a result of the electrical double layer of the object in a fluid (e.g. a zeta potential).

Figure 1:
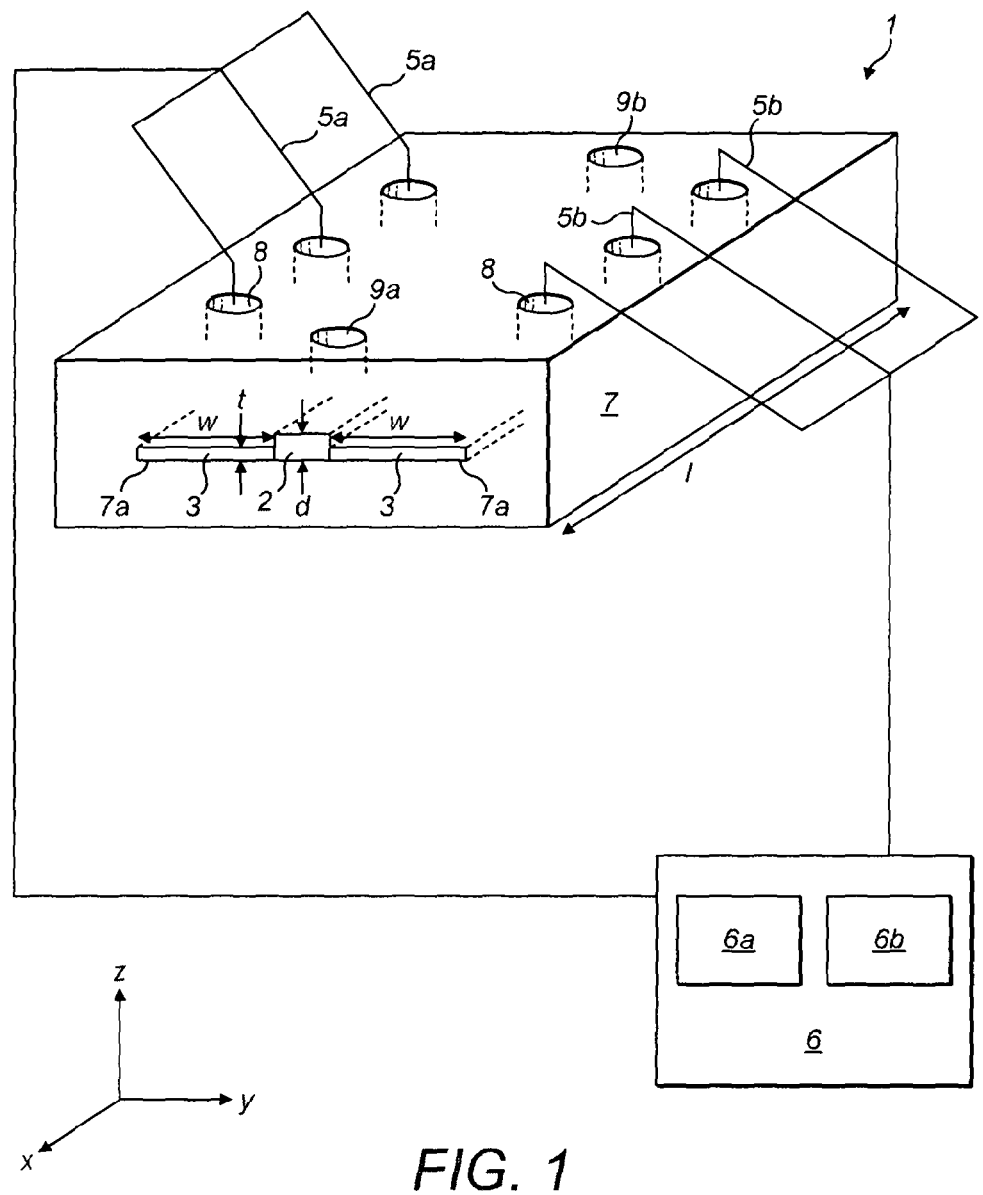
FIG. 1 is a schematic representation of a first embodiment of a device in accordance with the present invention.

FIG. 1 shows a device 1 in accordance with a first embodiment of the invention, comprising a conducting volume 2 in the form of a channel, which could be implemented in a capillary tube or on a microfluidic chip for example. The conducting volume 2 will be referred to as a channel 2 hereafter, but it will be understood that this is not intended to be limiting. Similarly, the relevant periphery of the conducting volume is taken to be a side of the channel extending along the length of the channel 2, although this is also not intended to be limiting.

The device 1 further comprises a field shaping electrical interface region 3 which, in this embodiment, consists of an ionically-conductive material 3 alongside and in electrical contact with the channel 2. In this example, since the electrical interface region 3 consists of one component only (the ionically conductive material), the region 3 will be referred to interchangeably as the "electrical interface material 3". This term will be used hereafter with reference to all but the third embodiment described below. However, this will be understood not to be limiting, since the electrical interface region 3 may comprise other components, in the form of additional ionic or non-ionically conducting materials, as will be described below in more detail in the exemplary third embodiment shown in FIG. 11.

The device 1 further comprises an electric field applying assembly which can comprise for example an array of spaced electrodes (e.g. a row) for applying an electric field to the material 3 along the channel 2, referred to below as 'write' electrodes 5a, and a controller 6. In preferred examples the electrodes are periodically spaced along the channel 2 but this is not essential.

An electric field measuring assembly, comprising for instance an array of 'read' electrodes 5b may, optionally, be provided for measuring the applied electric field. In this example, the 'read' electrodes measure the electric field from a second portion of electrical interface material 3 which is on the opposite side of the channel from the 'read' electrodes. However, other arrangements are possible as will be explained below.

The controller 6 may comprise a power supply unit 6b for generating individual voltages at the write electrodes 5a and a processor 6a which receives feedback voltages from the read electrodes 5b and adjusts the generated voltages in response to the received feedback. The controller could, for example, operate in the manner described in WO2006/070176 to generate voltages according to a desired field profile which is then varied over time. Alternatively, a non-shifting (i.e. time-constant) field of any desired shape could be applied. Examples of field profiles will be given below.

As will be described in more detail below, the channel 2 could take any shape including rectilinear, as shown in FIG. 1, or curved. In some embodiments, the channel can form a closed loop. Where the device 1 is an electrophoresis device for separating objects, the channel 2 can contain fluid which may be a buffer of choice, typically a conductive, aqueous buffer or a gel, for example. The pH of the fluid affects the apparent electrical charge exhibited by the objects to be separated and hence may be chosen dependent on the nature of the analytes to be separated in the channel 2, in order to provide optimum separation conditions. In the case of DNA or denatured SDS treated proteins, for example, the pH of the buffer is typically in the range 7.5 to 9. However, other pH ranges may be more suitable for other types of analyte—for instance, native proteins and metabolites are likely to require different pH conditions to achieve optimum separation. The pH of the conducting volume need not be constant throughout the device and if desired, it is possible to arrange different pH levels in different areas of the device. The objects to be separated are suspended within the fluid in the channel 2. A detector may also be provided for detecting events taking place within the channel. For example, any of the detector types described in WO2006/070176 could be utilised.

As will be described in more detail below, the electrical interface material 3 is ionically conducting (i.e. electrical current is conducted via ion movement) and may comprise a polymer of choice such as a hydrogel, for example, or a porous material such as porous glass, porous ceramic, foam or sponge filed with an electrolyte. It should be noted that the material 3 may itself be ionically conductive and/or could contain an ionically conductive substance, e.g. an aqueous buffer, within it. A suitable buffer which may be used is Tris-Borate-EDTA (TBE), preferably at a concentration within the range of 0.1× to 10× (typically, 10×TBE is obtained from a supplier and then diluted as required: for example, to make 1×TBE, a 1:10 dilution should be performed with deionised water. To make 10× concentrated stock solution of TBE from its components, the usual procedure is: weigh 54 g Tris base (formula weight=121.14) and 27.5 g boric acid (FW=61.83) and dissolve both in approximately 900 mL deionised water; add 20 mL of 0.5 M EDTA (pH 8.0)) and adjust the solution to a final volume of 1 L). It will be appreciated that TBE is an example and that other suitable buffer systems can also be used.

The electrical interface material 3 preferably has a moderate or high resistivity in order to avoid Joule heating and excessive electrolysis at the regions where electrodes are applied. However, it is preferable that the resistivity of the electrical interface material is comparable to that of the conducting volume 2 in order to achieve an appropriate degree of smoothing, as will be described in more detail below.

In this example, the electrical interface material 3 is located in a cavity 7a of a substrate 7 fabricated from an electrically resistive material such as glass or plastic. The cavity 7a is preferably designed such that it can be completely filled with the electrical interface material 3. In the device 1 shown in FIG. 1, the substrate 7 is provided as one integral piece and the channel 2 is provided inside the substrate 7, in the middle of the cavity 7a, e.g. by moulding during fabrication of the substrate. In other embodiments described in detail below, the channel 2 may be formed by the joining of two or more substrate pieces. In still other examples, the channel could be formed on an external surface of the substrate. The cavity 7a too can be internal or external.

In other examples, the electrical interface material could be applied to the device without containment within a cavity. For example, the material could be affixed to a surface of the device in a suitable location so as to contact at least an edge of the channel.

Where the electrical interface material is located inside the substrate, the electrode arrays 5a, 5b can be connected to several contact points on the cavity 7a via holes 8, also referred to as wells or well nodes. The holes shown in FIG. 1 are circular, although it will be appreciated that the holes may take any shape, including elliptical or rectangular. Each hole 8 provides access from the substrate surface to the upper or outer side internal wall of the cavity 7a, so that an electrode placed into the hole 8 makes direct electrical contact with the electrical interface material 3. In other examples, indirect electrical contact between the electrodes 5a, 5b and the electrical interface material 3 is achieved via the electric field applying assembly being provided with fluid-filled connection arms, as described below. Each hole 8 may also act as a well containing an ionic conducting solution (e.g. an aqueous buffer) for replenishing the electric interface material 3. Preferably, the reservoir size provided by the wells is sufficient to mitigate against ion depletion in the electrical interface material. For example, each well may be sized to hold a volume of around 1 mm$^3$.

In some configurations, a vent (not shown) could be located on top of the holes 8, to allow electrolysis gases to be vented whilst covering the wells to prevent spillage. Preferably, the vent is made out of made of a microporous material to repel the aqueous electrolyte inside the holes 8. This would be advantageous for packaged cartridge-like devices to prevent the prefilled contents (i.e. the electrolyte inside the holes 8) from leaking out. In some embodiments, the electrodes may be configured to pierce the vent upon set-up of the device.

The cavity 7a has a width (w) between the holes 8 and the nearest side of the channel 2 which is dictated by the spacing of write electrodes 5a and the desired degree of electric field smoothing. For instance, the holes 8 may be provided along the channel 2 at a distance typically ranging from 100 μm to several mm. The greater the width (w), the greater the degree of smoothing achieved. However, if the spacing of the write electrodes is small, a relatively low degree of smoothing (and hence smaller width (w)) may be sufficient. Preferably, the width (w) in the y direction is at least as great as, and preferably much greater than, the thickness (t) of the material 3 in the z direction. That is, the material has a "membrane"-like configuration.

In a typical example, the width (w) of the cavity 7a in the y direction is between 0.1 and 5 mm, while the spacing between electrodes along the channel in the x direction is around 3 mm, the length (l) of the cavity 7a along the channel in the x direction is several centimeters (e.g. 12 cm), and the thickness (t) of the cavity 7a in the z direction is between 1 and 100 μm. In some cases, it is desirable for the thickness (t) of the cavity 7a to be small, or at most equal to the depth (d) of the channel 2, so that the interaction between the analytes in that channel and the electric field interface material are minimised. For instance, for a channel 2 which is 10 to 100 μm deep and 20 to 200 μm wide, the cavity 7a is preferably between 1 and 100 μm thick (t) and 1 to 5 mm wide (w). In alternative embodiments, it may be preferable if the interface material 3 surrounds the channel 2, e.g. on all sides (including above and below), in order to achieve improved field uniformity in the y-z plane. Further exemplary dimensions will be provided below, with reference to the different methods of manufacturing devices in accordance with the present invention.

It should be noted that, in implementations which do not make use of a cavity for containing the electrical interface material, the above exemplary cavity dimensions apply equally to the electrical interface material itself.

In addition to the holes 8 for connecting electrodes, a number of well nodes serving as inlets and/or outlets 9a, 9b, may be provided for insertion and/or retrieval of fluid and/or analytes in the channel 2. In the case of a linear channel 2, as shown in FIG. 1, the two additional well nodes 9a, 9b are used for inserting additional write electrodes (not shown) forming part of the electric field applying assembly, which provide extra voltages in order to counter electric field edge effects, as described further below. These well node points can also serve as inlets and/or outlets.

Figure 2:
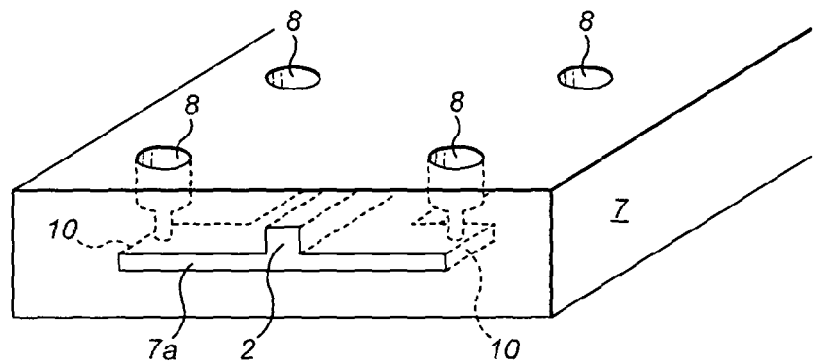
FIG. 2 schematically shows a portion of the device shown in FIG. 1.

As mentioned above, the electrodes 5a, 5b can be directly connected (e.g. via holes 8) to different points on the electrical interface material 3 in the cavity 7a, or indirectly, via connection arms 10, also referred to as a 'fluidic' arm 10, as shown in FIG. 2. Either way, the electric field applying assembly presents a discrete series of voltage points to the electric field interface material, giving rise to a discrete electric field profile. The "arms" 10 may be continuations of the material 3 or, alternatively, they may be filled with fluid only. In either case, each fluidic arm 10 preferably connects a single point voltage (e.g. only one electrode) to the electrical interface material 3.

Fluidic arms of this sort provide an extra degree of flexibility since their dimensions can be controlled to further adjust the voltage presented to the electrical interface material 3. For instance, by increasing the depth or lateral width of the arm, the electrical resistance it presents is reduced and the apparent voltage increased. In contrast, by increasing the length of the arm 10 (in the direction between the hole 8 and the material 3), the resistance is increased. This can be made use of in a number of ways. For instance, if the holes 8 are not all located at the same distance from the channel (as may be the case for example in "staggered" embodiments, of which an example is given below), the fluidic arms 10 may be sized to negate the effects of the different electrode positions on the electric field "seen" by the electrical interface material 3, e.g. by designing those arms 10 connecting the nearer electrodes to be narrower than those arms 10 connecting the farther electrodes. In this way, each arm 10 would present substantially the same resistance to each electrode, such that the voltage applied to the material 3 at each point would be reduced by a substantially equal amount, so as not to affect the shape of the field.

Alternatively, the fluidic arms 10 could take an active role in shaping the electric field applied to the material 3. For example, if the fluidic arms 10 are sized to present different levels of resistance, the same voltage could be applied to each electrode whilst still presenting the material with points at different voltages (and hence a non-zero electric field). In practice, some combination of the two approaches may be adopted.

A write electrode 5a dipped into the hole 8 therefore provides the requisite voltage for that interfacing point set by the controller 6. In this example, each opposing hole 8 contains a read electrode 5b to measure the voltages applied by the write electrodes 5a. Again, the read electrodes may be connected via fluidic arms 10, and the same considerations apply regarding their dimensions. The set-up shown is an example of an "asymmetric" design, wherein a row of write electrodes 5a is provided on one side of the channel 2, opposite a row of read electrodes 5b, and wherein the channel 2 is parallel to and in-between the two electrode rows 5a, 5b.

In preferred examples, the total width between the two opposing electrode rows may range from 1 to 6 mm and is typically around 2.2 mm. Accordingly, a typical exemplary width (w) of the electrical interface material 3 is 1 mm, with the electrical interface material 3 being provided at each side of a 200 μm wide channel 2. However, in practice, the electrical interface material 3 may be as narrow as 200 μm wide or less, and the channel itself could also be narrower than indicated above. The fact that there is no strict lower boundary on the width of the electrical interface material 3 is important if smaller devices are required, having less than a single micron or even nanometer-order dimensions. It will be appreciated that these are exemplary dimensions and the total width may vary, being higher for example in the case of multiple channel designs which will be described in detail below.

Figure 3:
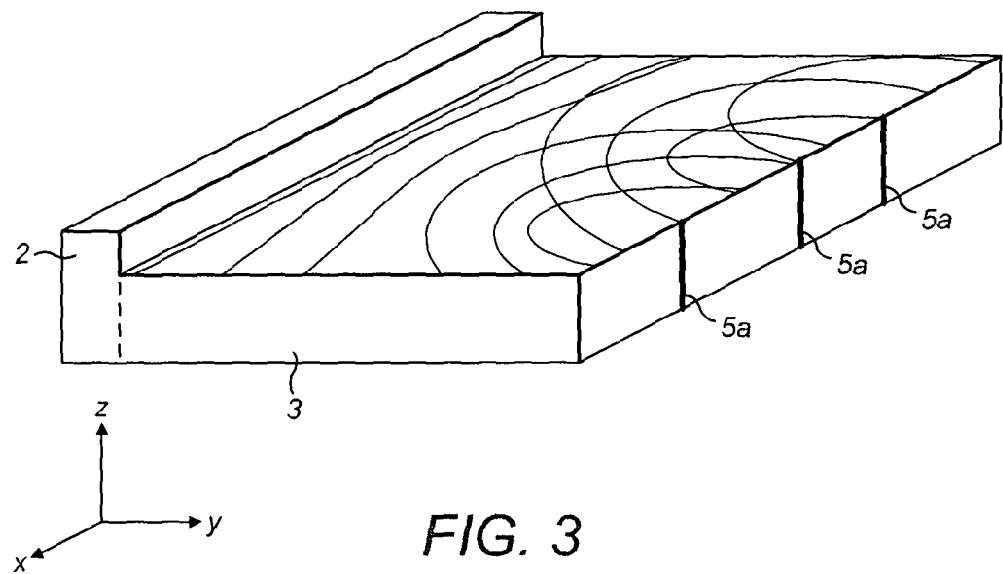
FIG. 3 is a schematic representation of the smoothing of the electric field profile via the electrical interface region.

FIG. 3 is a schematic representation of a portion of the device 1, showing a region of the electrical interface material 3 provided next to, and in electrical contact with, the channel 2. The contours shown in FIG. 3 schematically illustrate lines of constant voltage inside the electrical interface material 3. Note that in this example, purely for illustration, the same voltage has been applied to each of the illustrated electrodes however, in practice, different voltages will be presented in order to give rise to an electric field along the length of the channel 2. The voltage applied by each electrode 5a is ionically conducted between the points at which the electrodes 5a (or fluid arms 10) contact the electrical interface material 3 and the channel 2, with the equipotential lines decreasing in curvature as their radius increases. Ultimately, if the material dimensions are sufficiently large, the equipotential lines become substantially straight near the channel 2 which has the effect of smoothing the applied voltage. Where the voltages presented to the material 3 vary along the length of the channel (i.e. in the x-direction), at and adjacent to the location where the point sources are applied, a discrete electric field will be established. However, towards and at the channel 2, the smoothing effect of the material 3 means that a substantially continuous electric field is obtained inside the channel 2.

Figure 4A:
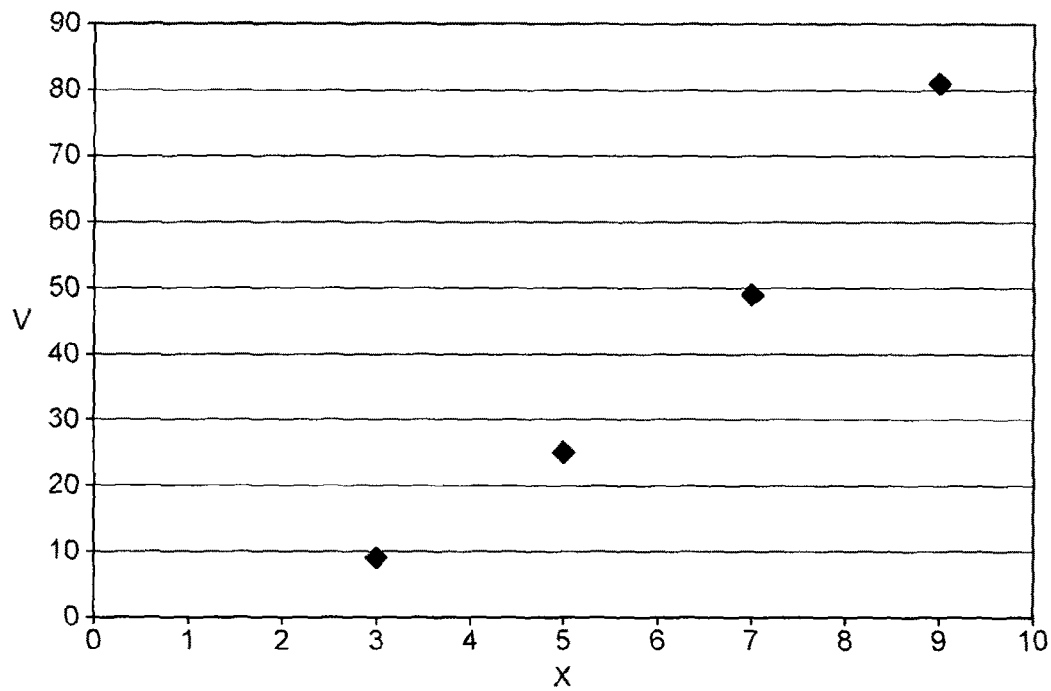
FIG. 4A is a graph of the voltage distribution corresponding to an exemplary discrete ('unsmoothed') electric field profile applied by an electric field applying assembly along a channel.
Figure 4B:
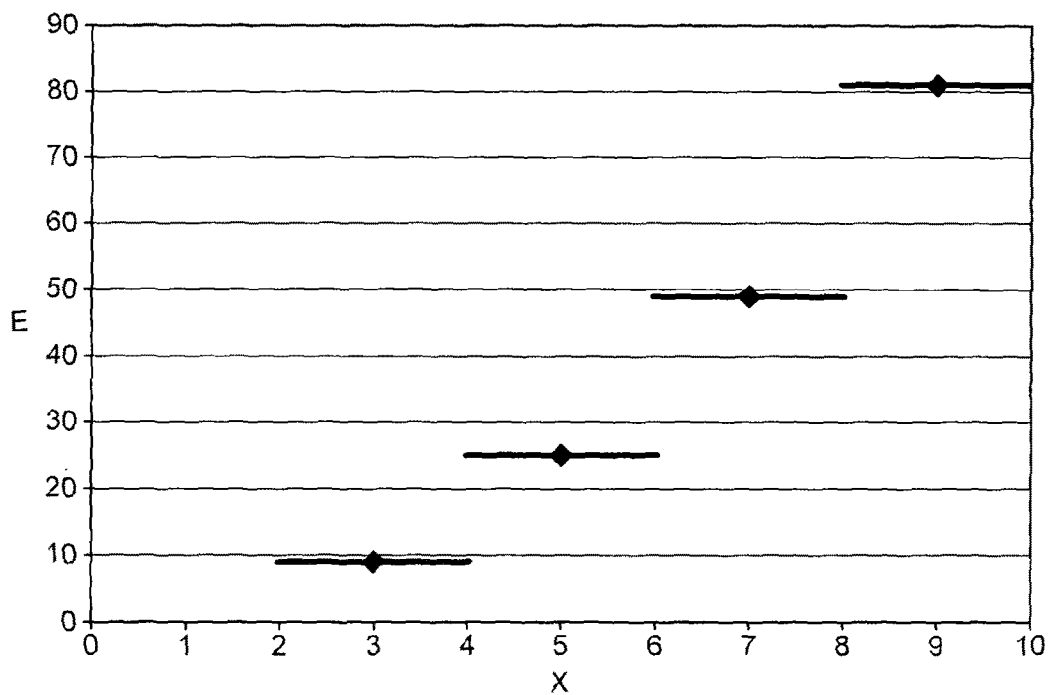
FIG. 4B is a graph of the discrete electric field corresponding to FIG. 4A.

FIG. 4A is a graph showing exemplary voltages V which may presented to the material 3 (e.g. by electrodes 5a) along a direction confirming to the path of the channel (in this case, along the x-axis). It will be seen that these are essentially point voltage sources, the magnitude of which is arranged to increase along the channel. In this example, the voltage is configured to increase in proportion to $x^n$, where n=2, although any other voltage variation could be adopted as appropriate to the application. The point voltages depicted FIG. 4A give rise to a discrete electric field E obtained along the channel as represented in FIG. 4B. It will be seen that the magnitude of the electric field increases step-wise, with each step representing a discontinuity in the field.

Figure 4C:
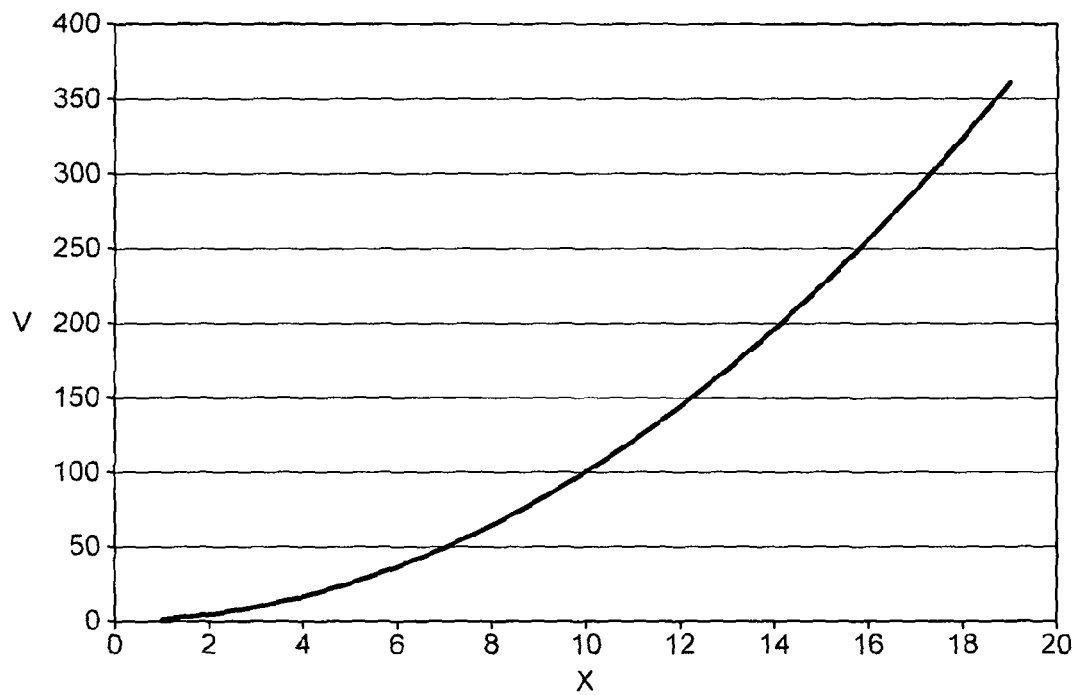
FIG. 4C is a graph of the voltage distribution corresponding to an exemplary continuous electric field profile obtained inside a conducting volume in the form of a channel when an electrical interface region is used to smooth the discrete electric field profile.
Figure 4D:
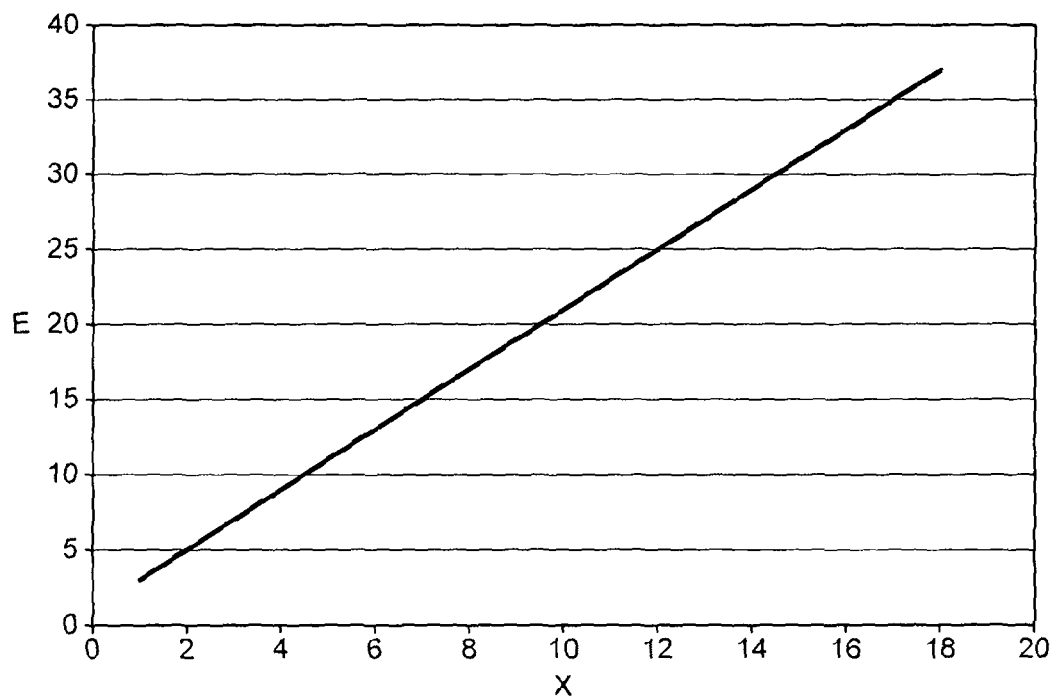
FIG. 4D is a graph of the electric field corresponding to FIG. 4C.

FIG. 4C is a graph showing exemplary voltages V which may be measured along the channel direction (x) adjacent to or inside the channel 2. It will be seen that the voltage distribution is now substantially continuous. The voltage distribution of FIG. 4C give rise to a substantially continuous ('smooth') electric field E obtained along the channel as represented in FIG. 4D. The particular continuous electric field E represented in FIG. 4D is linear (i.e. proportional to x), although it will be appreciated that it may be any substantially continuous function, depending on the particular voltage distribution applied to the electrodes.

In practice, the smoothed electric field may still contain a degree of discontinuity. For example, if the same parameters were applied in the example above, but the width of the material 3 were reduced significantly, the smoothing would not be complete and hence the electric field established in the channel would be a modified step function rather than a straight line. However, it would still be more continuous than the original discrete applied field.

As already noted, the electrical interface material 3 is selected to have suitable ion transport characteristics to allow an electrical connection between the electrodes 5a and the channel 2. If, in contrast, the material primarily conducted electricity via the movement of electrons (or holes) it would act as an electrode and support electrochemical reactions at its surface and in the process produce gas bubbles from electrolysis. These bubbles would seriously disrupt the electric field obtained in the channel 2 and consequently the operation of the device 1. This is avoided through the use of an ionically conductive material 3. Preferably, the electrical interface material 3 has suitably rapid ion mobility, so that ion depletion does not become excessive during use.

The conductivity and relative dimensions of the interface material 3 should be such that, in use, the current flow is not excessive, in order to avoid Joule heating and excessive electrolysis at the electrode well nodes.

As mentioned above, the ionic conductivity of the interface material 3 should preferably be such that it is comparable to that of the filled channel 2 (typically a buffer or gel). If the conductivity of the interface material 3 is too high or too low, the electric field shape may not form as desired in the channel 2. This is because, if the relative conductivities of the fluid inside the channel 2 and the electrical interface material 3 were significantly different, then Ohm's law predicts that all the current would pass predominantly through the electrical interface material 3 or predominantly through the channel 2, thereby altering field smoothing effects (i.e. over-smoothing or under-smoothing). In addition, if the conductivity of the material 3 is too low, the electric field obtained in the channel 2 may be damped, i.e. appear much lower than the intended field applied at the electrodes 5a, because the power is essentially lost in the electrical interface material 3. Accordingly, it is preferable that the relative resistivities of the channel 2 and of the electric field interface material 3 be taken into account in order to achieve the desired field in the channel 2. In a preferred configuration, the relative resistivities are of the same order. In particularly preferred cases, the conductivities/resistivities of the channel 2 and material 3 differ by a factor of no more than 100, preferably no more than 50, most preferably no more than 10.

However, in practice this can be difficult since where the device is an electrophoresis device, the conductivity/resistivity of the fluid within the volume is limited in range. This is because the fluid must be of a suitable composition (in terms of pH and concentration) to give rise to suitable separation conditions. As such the conductivity of the fluid is constrained and is typically relatively high in comparison to preferred conductivities of the electrical interface material (which are ideally kept moderately low as mentioned above). Therefore it may not be practicable to arrange for the conductivities of the fluid in the channel 2 and the material 3 to be very close, although any difference is preferably kept to the minimum possible. The magnitude and/or shape of the applied electric field may be adjusted to take the resulting effects into account.

The resistivity of the electrical interface material 3 may be constant throughout its volume, and this is preferable in order that a homogeneous electrical interface material 3 may be employed. This will give rise to isotropic field smoothing in the material. Alternatively, in other embodiments, it is desirable that the resistivity of the electric field interface material varies in at least one direction. For example, the resistivity/conductivity of the material 3 could vary along the length of the channel (in the x-direction, in this example) in order to introduce additional field-shaping effects. In other examples, the resistivity/conductivity may vary in the direction perpendicular to the channel path (here, the y-direction) and an example of this will be given below.

The resistivity of the electrical interface material may be varied by introducing pillars (not shown) in the cavity 2 and varying either their diameter or their density in one direction. This has the effect of removing conducting material and thus increasing the resistivity of the electric field interface material 3 (or reducing it if the density of the pillars drops). Alternatively, the composition of the material itself may be varied. For instance, in the case of a hydrogel (described below), the density of its pores and/or ion channels may be engineered to vary from region to region. As another alternative, the thickness of the electrical interface material may be varied across its width.

It is also desirable that the electrical interface material 3 is impervious to gas bubbles produced by electrolysis in the electrode holes 8 in order to avoid these bubbles disrupting the transport of ions within the material and so distorting the electric field. It is further desirable that the electrical interface material 3 be impervious to any analytes contained in the channel 2.

Additionally, the electrical interface material 3 should be sufficiently robust, chemically and thermally stable and inert. It is also important that the material 3 be stable in an electric field and not significantly distort physically or change its electrical or physical properties. It is also desirable that the electrical interface material 3 suitably adheres to the cavity 7a inside the substrate 7 and does not allow appreciable sticking of any analytes inside the channel 2 to its surface.

A particularly suitable material which can be designed to meet all of the above criteria is a hydrogel. Hydrogels are a class of polymeric materials that are able to absorb aqueous solutions but do not dissolve in water. A hydrogel forms a network of pores or channels which can contain fluid and through which ions in the fluid can pass. This property arises from the fact that the three-dimensional networks of polymer chains are held together by physical and/or chemical crosslinkage, wherein the spaces between these macromolecules are filled with water. Depending on the properties of the polymers as well as the nature and density of the network used to form the hydrogels, such structures are able to contain various amounts of water. Typically, the pores and/or channels are of such small dimensions that the material may be referred to as nanoporous. Where a hydrogel is used as the electrical interface material, it is preferably the fluid carried within the channels/pores which conducts electrical charge (via ion transport) through the material. The intrinsic hydrogel itself is preferably substantially electrically insulating. Hence, hydrogels have many attractive attributes that make them highly suitable for use as an electrical field interface for smoothing the shape of electric fields. It will be appreciated however that any type of ionically conductive material that meets the specified criteria may be used.

There are two general classes of hydrogels. The physical gels, or pseudogels, consist of polymeric chains connected by electrostatic forces, hydrogen bonds, hydrophobic interactions or chain entanglements. Such hydrogels are held together by non-permanent forces or bonds and therefore they can usually be converted back to polymer solutions on heating. The chemical hydrogels, also known as true or permanent hydrogels, on the other hand, are held together via covalent bonds between the chains. Either hydrogel type could be used in the presently disclosed device.

Preferably, the electrical interface material 3 is compatible with the material that the substrate 7 is made from. The substrate 7 is typically fabricated for example from glass, fused silica, quartz or plastics such as poly(methyl methacrylate) (PMMA) or cyclic olefin copolymer (COC), or from an elastomer such as polydimethysiloxane (PDMS).

Furthermore, when selecting the electrical interface material 3, consideration must be given as to whether it may be easily incorporated into the device 1. A liquid polymer (e.g. an uncured hydrogel) material may be introduced into the cavity 7a of the substrate 7 via inlets 9a, 9b (e.g. by injection) and polymerised in situ using for example photo-initiation (e.g. by UV radiation) or by thermal means to form the electrical interface material 3. This will be described in more detail below.

The substrate 7 itself may be fabricated using selected microfabrication procedures, some examples of which will now be explained. Ideally the material used to manufacture the substrate 7 is transparent to ultraviolet radiation for subsequent photo-patterning and photo-polymerisation. This is also beneficial for detecting events within the channel. The substrate may also be transparent to visible light for this purpose.

Figure 5A:
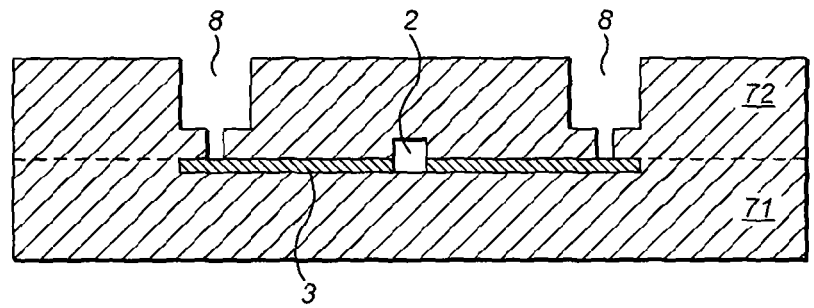
FIGS. 5A, 5B and 5C respectively depict cross-sectional views of further embodiments of devices in accordance with the present invention.
Figure 5B:
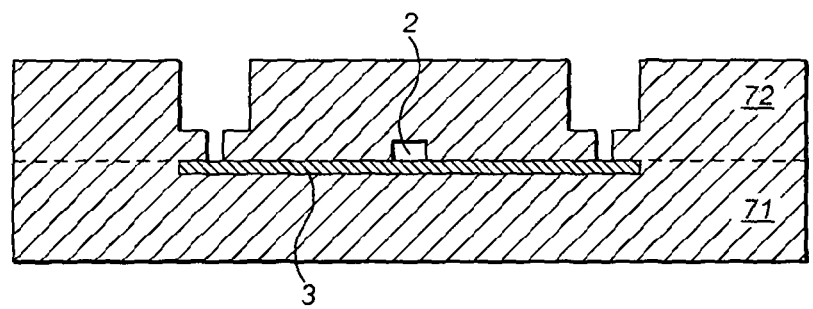
Figure 5C:
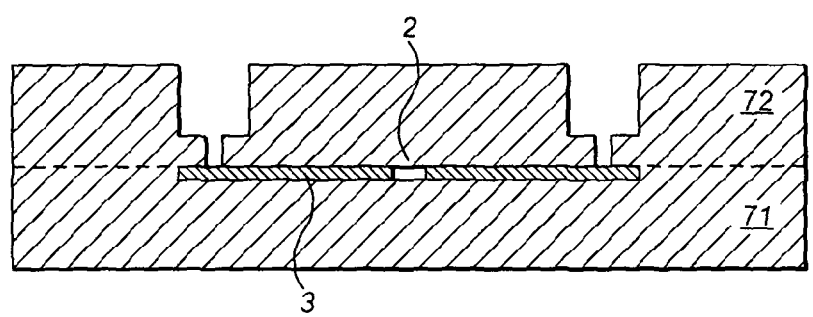

The channel 2 and the cavity 7a, could be formed within a single substrate piece, as shown in FIGS. 1 and 2, e.g. by machining or moulding. Alternatively, recesses from which the channel 2 and the cavity 7a may be formed are provided on separate plates 71, 72 which are then affixed together to form the substrate 7, as shown in FIGS. 5A to 5C. Either or both plates 71, 72 can contain the electrode connection points and one piece (generally the top plate 71) has holes 8 drilled, blasted, cast or moulded for example with the appropriate equipment. The fabricated plates 71, 72 are then bonded together typically using a hot press, plasma chamber, furnace, ultrasound, solvents, suitable adhesives or by any other conventional bonding method described in the literature to form a closed system.

The channel 2 can be made by etching, machining, hot embossing, injection moulding, casting, ablating or otherwise forming a guide channel which is physically delimited by surfaces of the substrate—however, as will be seen below this is not essential. In one case, depicted in FIG. 8A, the channel 2 may be formed in a top piece 72 of the substrate 7, to a typical depth of around 20-40 µm. The cavity 7a, formed in a bottom piece 71 of the substrate, is another 20-40 µm thick. Once the two plates are affixed together, this makes the total channel depth 40-80 µm as it includes the cavity thickness, as shown in FIG. 5A.

In another example, both the channel 2 and cavity 7a can be formed on the surface of one plate 72, as shown in FIG. 8B, and affixed to a second plate which may or may not be provided with further recesses.

FIGS. 5C and 8C show an example in which no physical guide channel is formed to define the channel 2, and instead the channel 2 is ultimately contained entirely within the same cavity 7a which holds the electrical interface material in use. The sides of the channel 2 are defined by the electrical interface material itself.

If the substrate material is plastic, the channel 2 and cavity 7a can be micro-machined in each substrate plate 71, 72 by a suitably accurate machining tool or computer numerical control (CNC) machine, stamped using a mould/tool and hot embosser, photo-patterned using another liquid polymer material, selectively melted and vaporised by a sufficiently powerful laser, or by any suitable method described in literature. If the substrate material is glass, fused silica or quartz the channel 2 and cavity 7a are preferably etched using standard hydrofluoric acid etch procedures or deep reactive ion etching. Glass for example may be machined, laser or electrochemically etched, or sand blasted.

Another alternative fabrication method suitable for forming the device is 3D printing. These are self contained systems able to form miniaturised structures at very high resolution. The devices described herein could be fabricated with such a system, for example using photopatternable polymers, optionally including the direct deposition and incorporation of the interface material (e.g. hydrogel).

The cavities formed in the substrate may be treated in order to prevent sticking of the analytes of interest present inside the channel 2 during analysis to the inner walls or inner surface of the conducting volume. For example, the inner walls or surface of the conducting volume may coated with a suitable material such as a polymer. The surface of the cavity which is to be filled with the electrical interface material 3 may be silanised to improve adhesion of the material 3 to the substrate, or coated with any other suitable adhesion promotion system. The coating or silanisation may be selective to enable patterning of the material.

The holes 8 can be mechanically drilled or ablated by laser or sand, or by any suitable technique in the literature. Typically the substrate pieces 71, 72 are then correctly aligned and bonded.

The electrical interface material can be inserted in a number of ways. In some cases, the electrical interface material could be provided in a solid, already-cured form. In this case, the material could simply be placed within the cavity 7a, for example before the two plates 71, 72 are bonded together. Also in examples where there is no cavity this may be the preferred option—for instance, the material could be adhered to a surface of the substrate alongside the cavity.

However, in preferred examples, the electrical interface material is introduced to the device in fluid form (e.g. a prepolymer). This has been found to result in a better bond between the substrate and the material, leaving few or no gaps at the interface for analyte or gasses to pass through. If the material is to be arranged on an outer surface of the device, or introduced to one or other of the plates 71, 72 prior to their being bonded together, the material can be coated onto the surface or into the cavity by any convenient method including printing, spreading, spin-coating etc. If the material is to be introduced into an already-made internal cavity, then injection methods are preferred. For instance, the material could be injected through any of the holes 8 described earlier.

One particularly preferred technique for introducing the material 3 in fluid form utilises capillary forces acting on the electrical interface material 3 due to the small dimensions of the cavity 7a. If the cavity 7a (and any guide channel) provided in the substrate are of suitable dimensions, upon introduction, the electrical interface material 3 fills in the cavity 7a whilst leaving a region constituting channel 2 (located above and within the cavity 7a) substantially free of interface material, as shown in FIG. 5A. In order for the capillary effect to work well, the inventors have found that the depth of the guide channel 2 provided above the cavity is, preferably, approximately equal to the thickness of the cavity 7a. Accordingly, in the case of a physically machined or etched channel 2 with electrical interface cavity filling by capillary action, this results in the total depth of the channel 2 being approximately twice the thickness of the cavity 7a (and therefore approximately twice the thickness of the electrical interface material 3 filling the cavity).

Figure 6A:
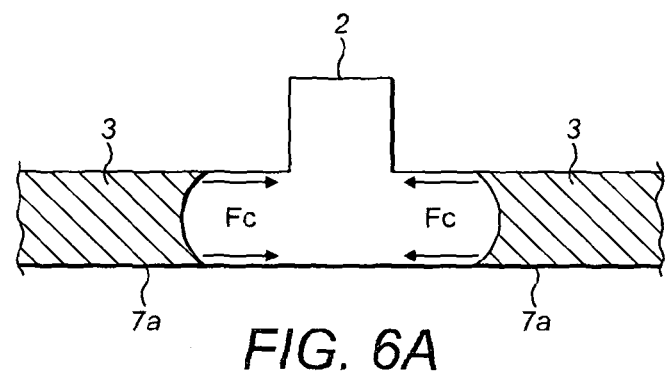
FIGS. 6A and 6B illustrate the formation of a channel by capillary forces.

FIGS. 4A and 4B schematically show the way in which the channel 2 is formed via capillary action. Capillary forces $F_c$ shown in FIG. 6A act on the surface of the electrical interface material 3 in liquid form inside the cavity 7a representing a 'container' for the liquid material 3. Under the influence of the capillary forces, $F_c$, the liquid material 3 reaches the region of the channel 2 and then stops flowing. For example, depending on the relative hydrophilicities of the surfaces and liquids involved, the liquid material may form a (concave or convex) meniscus in the cavity 7a either side of the channel 2 provided above the cavity, as shown in FIG. 6, although this is not always the case.

Figure 6B:
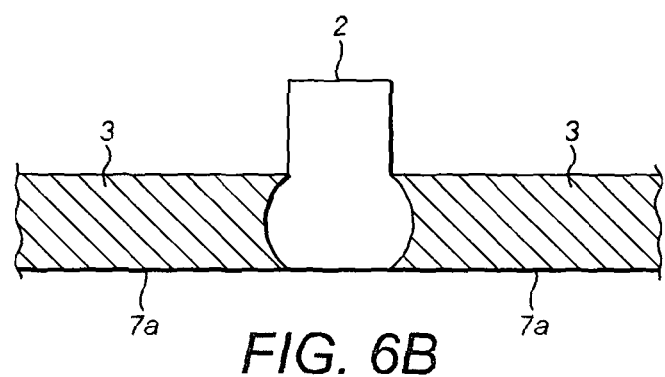

The capillary forces $F_c$ cause the liquid material to fill the cavity 7a, drawing the liquid material 3 in a direction towards the channel 2, either side of the channel 2. As shown in FIG. 6B, the capillary forces $F_c$ act on the material 3 until the liquid material 3a reaches the channel 2, where the capillary forces stop acting on the surface of the liquid material 3 due to the increased size of the 'container' surface (which now includes the channel 2). The electrical interface material 3 can then be solidified, e.g. by polymerising the prepolymer. This may be achieved by light irradiation, thermal means or room temperature chemical reaction, for instance.

Where the electric field applying assembly is to include connection arms 10, the dimensions of the arms may be determined in part on the same principles described above for capillary filling of the cavity. For instance, if it is intended that the arms 10 are to be filled with fluid and not with the electrical interface material 3, the dimensions of the arms may be configured such that capillary action does not draw the fluid material 3 into the arms 10. For example, the depth or lateral width of the arms 10 may be chosen to be large enough relative to the dimensions of the cavity such that the electrical interface material 3 is prevented from entering the fluidic arms 10. On the other, hand, if it is intended that the arms 10 be continuations of the electrical interface material 3, the depth or lateral width of the arms 10 may be decreased, so that the capillary forces do force the electrical interface material to enter the arms 10.

Figure 7A:
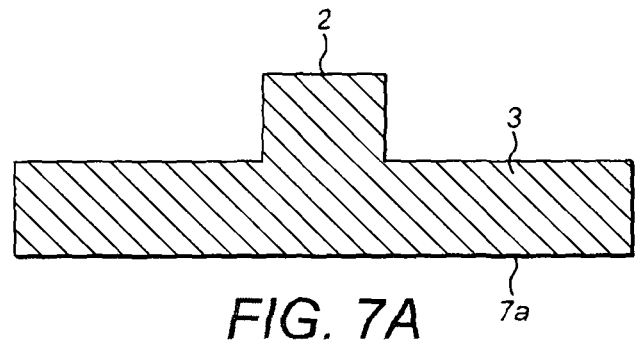
FIGS. 7A to 7C illustrate a technique for providing an electrical interface region and a channel inside a substrate.
Figure 7B:
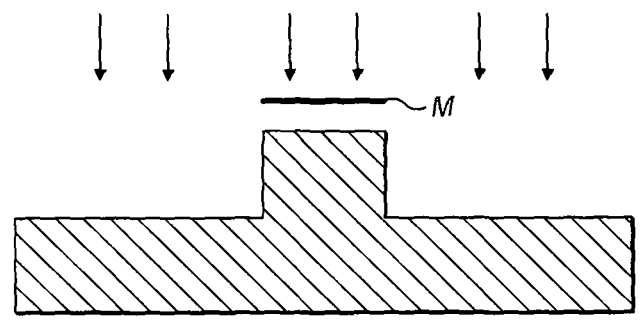

In another example, the electrical interface material can be formed whilst maintaining a channel 2 by taking advantage of the photo-patternability of an interface material 3 comprising a liquid prepolymer for example. In one such case, the substrate plates 71, 72 shown in FIG. 5B are transparent to light, for example to UV radiation. After their fabrication, the substrate pieces are fabricated, bonded and filled with a liquid prepolymer. The channel 2 and cavity 7a filled with the liquid prepolymer are schematically shown in FIG. 7A. The electrical interface material 3 is then created from the liquid prepolymer using a light mask, which selectively masks regions above the substrate.

Figure 7C:
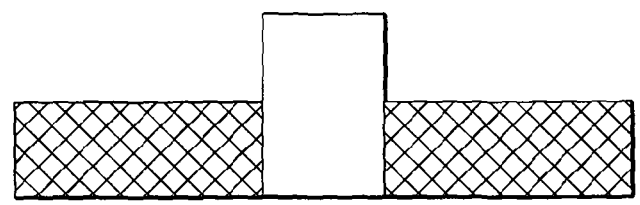

FIG. 5B shows a light mask M above the channel 2, wherein the mask M is substantially opaque to UV radiation applied to the substrate, in a direction perpendicular to the substrate by a laser or similar light source. It will be appreciated that any light source of appropriate energy (wavelength) to initiate polymerisation in the liquid prepolymer may be used, and the mask M need only be opaque to the particular wavelength chosen. Alter polymerisation, any unpolymerised material (i.e. material present under the mask) may be removed from the substrate, e.g. by passing fluid (i.e liquid or gas) through the channel 2 to flush out the uncured material. Alternatively a low pressure or vacuum may be applied to draw out the uncured material. FIG. 7C shows a resulting channel 2 being formed by removing the unpolymerised material which was located under the light mask. In practice, flushing may not remove all of the material and a region of interface material may remain in the channel, as depicted in FIG. 5B. However this is not problematic.

The same photo-patterning principles can be used to create a channel 2 where no guide channel is initially formed in the substrate and the whole cavity 2 is filled with the pre-cured material. As shown in FIG. 5C, the walls of the channel 2 are then defined by the material 3 itself. It will be appreciated that, in the case of a channel 2 obtained by photo-patterning in this way the electrical interface material 3, the depth of the channel 2 can be approximately equal to the thickness of the cavity 7a, as no guide channel physically provided or etched in the substrate is required (i.e. the channel 2 is merely a space in the electrical interface material 3 under the region which was shadowed by the mask M).

In other examples, the polymerised interface material 3 may be chemically or mechanically etched, ablated or machined to remove it from the channel region.

A substrate 7 which is fabricated, bonded, and comprising electrical interface material 3 inside the cavity 7a is usually referred to as a chip.

Depending on the application, once the chip is formed, the channel 2 may be filled with any material, typically fluid, appropriate for the type of procedure which is to be performed on the chip. (Note that the fluid may be omitted if the device for certain applications, e.g. if the device is not an electrophoresis device.) The channel 2 may be filled via inlets 9a provided in the top piece 71 of the substrate 7. For example, the fluid filling the channel 2 may be designed to offer differing resistances to the analytes of differing charge to mass ratio or just different size depending on the sieving material that are inserted into the channel 2 (commonly known as a separation gel or sieving matrix). This may be any liquid such as water/buffer, or any separation gel system such as polyacrylamide, poly(vinylpyrrolidone) (PVP) or hydroxyethyl cellulose (HEC). Alternatively, the conducting volume may be filled with micelles, or packed with a porous polymer monolith, chromatographic gel (e.g. cyclodextrins) or a bed of particles, to take advantage of size exclusion and or affinity separation processes.

The chip may be then interfaced with the write and read electrode arrays 5a, 5b which connect the chip with the controller 6. The controller 6 comprises a processor 6a which includes software controlled electronics to provide electric field shapes as required in the analysis. For example, the controller 6 may provide field shifting in the form of a suitable time dependent field gradient along the channel 2. When the shifting electric field is applied via the electrical interface material 3, any analytes confined in the channel 2 are subjected to the electric force due to the electric field obtained in the channel 2, which has a smooth, continuous shape.

If an electric field measuring assembly is provided, such as the 'read' electrode array described above, the controller 6 may perform feedback, using the measured electric field to adjust the applied voltages so that the desired electric field is achieved.

Devices in accordance with embodiments of the present invention may be separation devices for separating objects wherein the channel 2 contains objects to be separated. The substantially continuous electric field obtained in the channel 2 gives rise to an electric force acting on each object. A balancing source, as exemplified below, may be used to give rise to a force opposing the electric force on each object so that the objects in the separation channel are caused to separate under the combined influence of the electric field and the balancing source.

For example, the device may be an electrophoresis device, wherein the balancing source is a fluid contained in the channel together with the objects to be separated. In the case of an electrophoresis device, under the combined influences of the electric force and a hydrodynamic force due to the fluid in the channel 2, analytes inside the channel of suitable dimensions can separate into 'bands', the width and separation of which are dependent on the applied field conditions. The device may also be extended to selectively remove and/or sort analytes for downstream analysis after being concentrated into bands, e.g. using mass spectrometry or other analytical method to determine the composition of each band. An example of an arrangement which could be used for this purpose is illustrated in FIG. 15B, described further below.

It will be appreciated that devices in accordance with the invention are not restricted to the above applications, which are merely exemplary.

If a detector is provided for detecting events within the channel, the processor 6b may also be configured to analyse the data collected. For example, the controller 6 may analyse visual data (typically light from fluorescently labelled biomolecule analytes) for example from a microscope, spectrometer (for example to perform Raman spectroscopy), photodiode array, charge-coupled device (CCD), photomultiplier tube (PMT) or similar wavelength selective device in which the chip is placed in proximity to or integrated with. This can also be data from non visual electromagnetic radiation analysis methods. Other non-electromagnetic detection methods such as localised changes in conductivity, radiation, and refractive index changes may also be used for detection of analytes inside the channel 2. This is described more fully in WO2006/070176.

Figure 9:
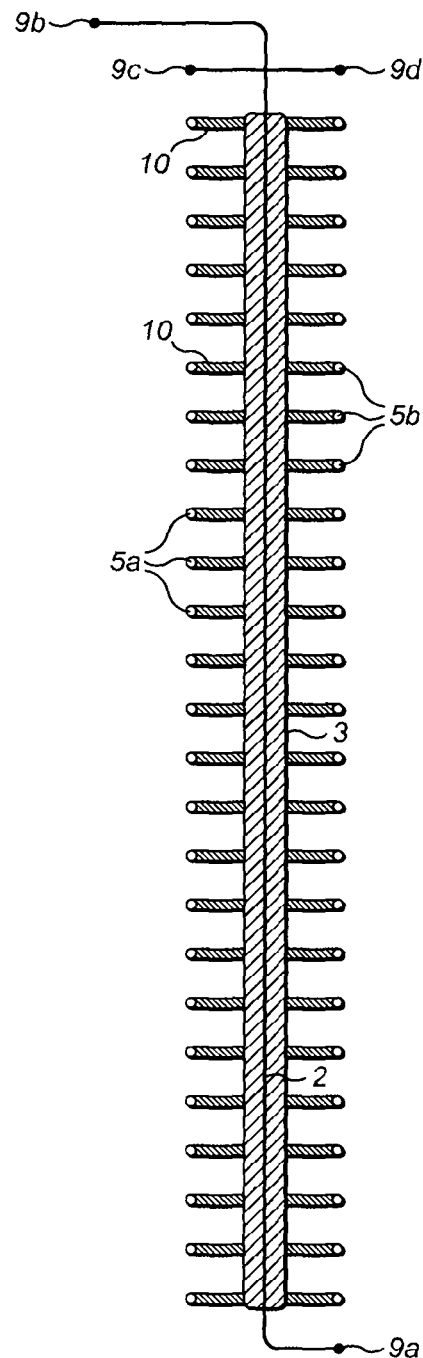
FIG. 9 is a plan view of the first embodiment, having a conducting volume in the form of a linear channel and electric interface region positioned along both sides of the channel.

As mentioned above, the FIG. 1 embodiment is a so-called "asymmetric" implementation, and FIG. 9 shows a schematic plan view of the same for further explanation. In this example, the row of write electrodes 5a is opposite the row of read electrodes 5b, with the channel 2 in-between, wherein the channel 2 is parallel with the two rows 5a, 5b and separated by the electrical interface material 3. The electrodes 5a, 5b are connected to the electrical interface material 3 via connection arms 10.

Figure 10:
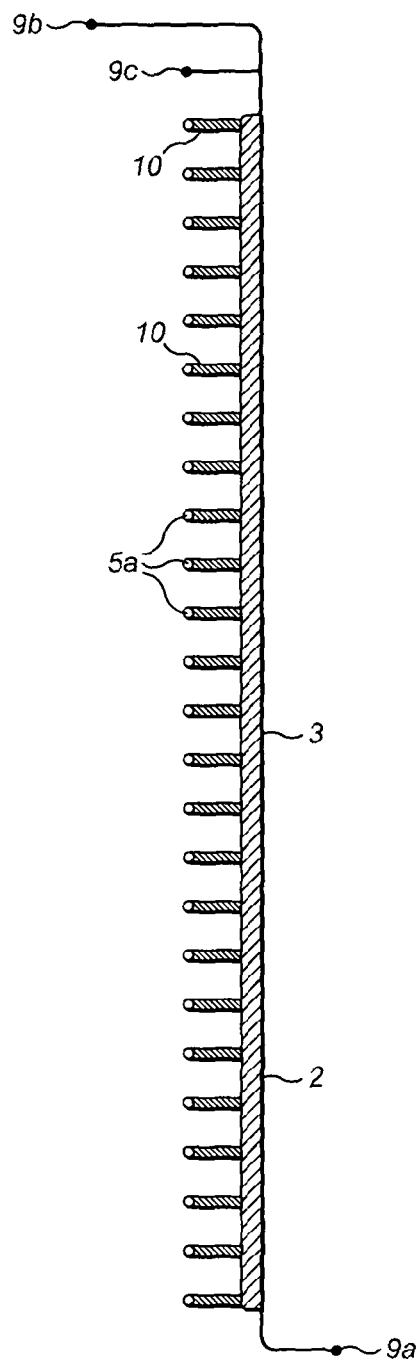
FIG. 10 is a schematic representation of a second embodiment having a conducting volume in the form of a linear channel and electrical interface region positioned along only one side of the channel.

However, as indicated already, the provision of read electrodes (or any form of electric field measuring device) is optional and FIG. 10 is a schematic representation of a second embodiment, which does not contain read electrodes. In this configuration, the electrical interface material 3 is present only on one side of the channel, between the channel 2 and the array of write electrodes 5a. If it is desired to monitor the established electric field, this can be achieved through the write electrodes 5a. For example, for short intervals (e.g. one microsecond every 100 ms, although in practice the cycle may depend on the velocity of the electric field, in a time-shifting electrophoresis system), the voltage supply to the write electrodes 5a can be switched off and, instead, the same electrodes used to obtain a measurement of the voltages at each location along the channel 2. Provided the measurement interval is sufficiently short, this has no substantive effect on the motion of analytes inside the channel 2.

Figure 11:
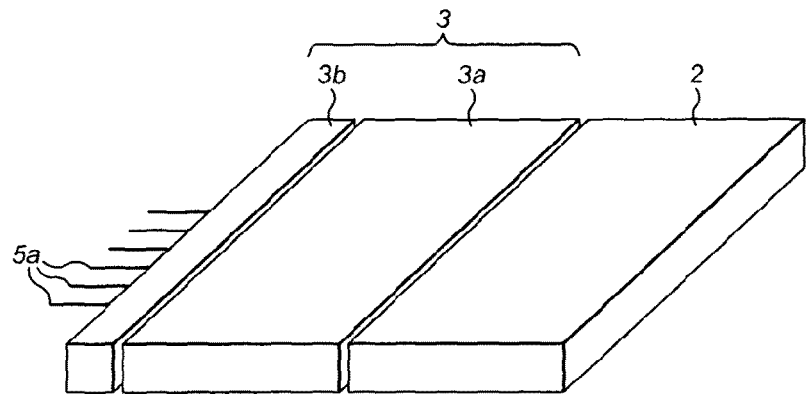
FIG. 11 is a is a schematic representation of a third embodiment having an electrical interface region consisting of an ionically conductive material and a non-ionically conductive material.

FIG. 11 is a schematic representation of the electrical interface region 3 and conductive volume 2 in a third embodiment, wherein the electrical interface region 3 comprises an ionically conductive material 3a and a non-ionically conductive material 3b. It will be noted that FIG. 11 does not depict the other components of the device, such as a substrate, but these can be provided in the same manner as discussed above in relation to the previous embodiments. The ionically conductive material 3a may be any suitable material as described above with reference to the 'electrical interface material' in the first two embodiments, for example a hydrogel. The non-ionically conductive material 3b, for example an electrically conductive material, may be a resistive polymer, a semi-conductor or even a metallic material.

It will be appreciated that any non-ionically conductive material may be used. The ionically conductive material $3a$ is located between the non-ionically conductive material $3b$ and the channel 2. In this embodiment, the write electrodes $5a$ are directly in contact with the non-ionically conductive material $3b$.

Preferably, the conductivity/resistivity of the non-ionically conductive material $3b$ and the conductivity/resistivity of the ionically conductive material $3a$ are "matched". By "matched" it is meant that both conductivities are taken into account alongside the shape and magnitude of the applied field, such that both the non-ionically conductive material $3b$ and the ionically conductive material $3a$ contribute to the smoothing of the discrete electric field applied by the electrodes $5a$ to the non-ionically conductive material. In preferred configurations, the conductivities/resistivities are of the same order of magnitude. The ratio of the two materials' conductivities/resistivities is preferably between 100:1 and 1:1.

In the embodiment shown in FIG. 11, electrodes $5a$ may be connected to the material $3b$ instead of being dipped in fluid wells as described above with reference to the first two embodiments. Advantageously, this results in a more coherent and sealed device. However, the interface between the ionically conductive material $3a$ and the non-ionically conductive material $3b$ (which are in electrical contact) is typically fluid/solid, which tends to give rise to electrolysis and evolution of gas bubbles. Pores, wells or tracks (not shown) may be provided in the substrate at this interface to act as exhausts for the gas bubbles. Advantageously, the ionically conductive material $3a$, located adjacent to the channel 2, is impervious to gases from electrolysis thereby preventing them from reaching channel 2.

Figure 12:
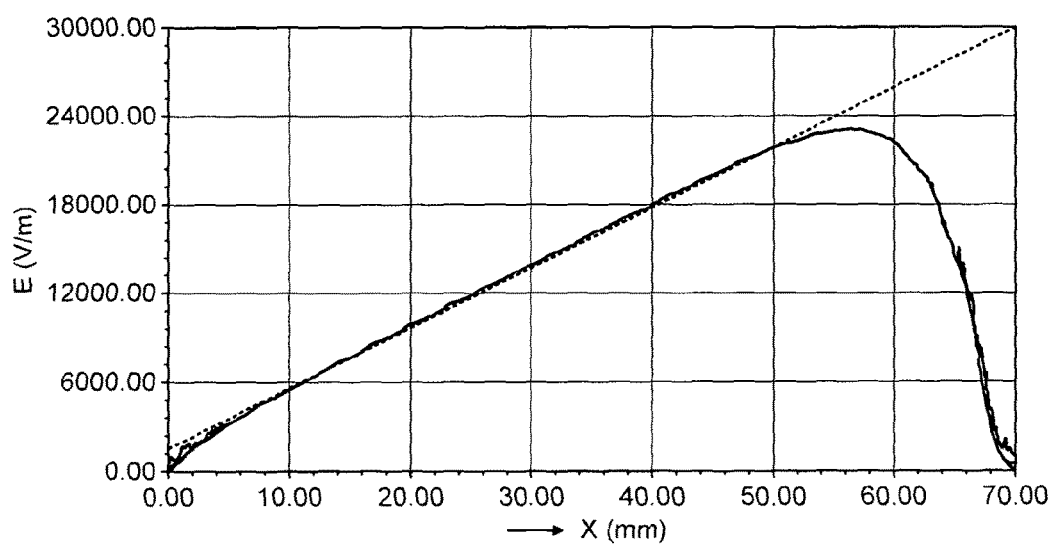
FIG. 12 is a graph illustrating an exemplary electric field profile along a conducting volume in the form of a linear channel.

Devices shown in FIGS. 9, 10 and 11 for example have a single linear channel 2, which has a beginning and an end. There are several disadvantages with such "open loop" configurations. Firstly, the ends introduce field edge effects, where the electric field obtained inside the channel 2 at either end of the device deviates from the desired level. An example of this effect is illustrated in FIG. 12. The desired electric field has a linear profile as indicated by the dotted line, while the actual electric field obtained in the channel 2 deviates from this line, as represented by the solid-line curve. This is due to asymmetric field averaging as the end of the electric field applying assembly is approached. The field flattening observed in the solid-line curve close to the channel ends means that a significant portion of the device cannot be utilised for analysis.

Secondly, when performing field-shifting operations with an open loop system, regions can occur where the field varies very little and the electric current direction remains essentially unchanged, for significant periods of time. This can lead to severe localised ion depletion in the electrical field interface material 3. As a result, the desired field shape in the channel 2 may be lost since the effects of ion depletion tend to counteract the applied field. In serious cases, this can lead to non-linear electrophoretic effects and the formation of electro-osmotic flow vortices, which are highly detrimental in analyte separation procedures. Thirdly, when an open loop system is utilised, its effective operational length is dictated by the physical length of its channel 2.

Figure 13:
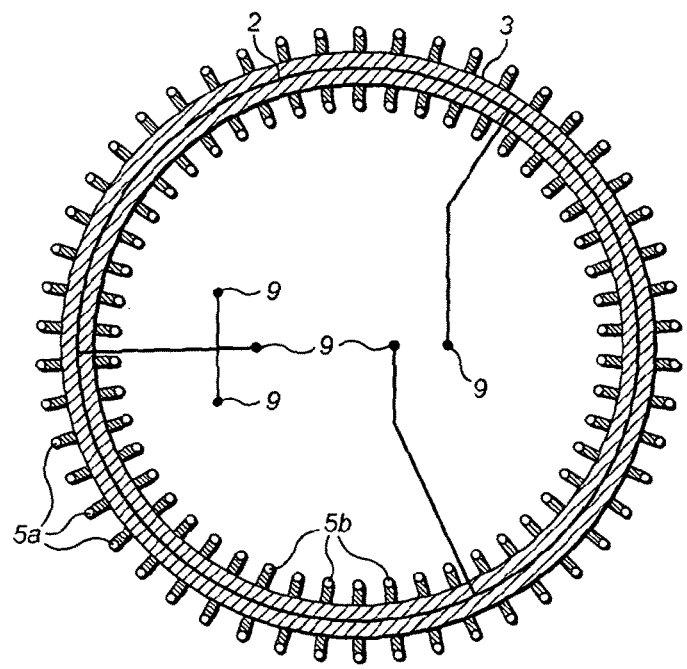
FIG. 13 is a schematic representation of a third embodiment, having a conducting volume in the form of a circular channel.

In a third embodiment, the disadvantages listed above may be overcome by using closed loop configurations, for example a circular channel 2 as shown schematically in FIG. 13. The circular channel 2 is connected to a set of write electrodes $5a$ and an (optional) set of read electrodes $5b$, via an electrical interface material 3. The circumference of the channel 2 may be for example between 100-200 mm, typically 120 mm.

The write electrodes $5a$ are periodically spaced along a circle concentric with the circular channel 2, with a radius greater than that of the circular path of the channel 2. Similarly, the read electrodes $5b$ are periodically arranged in a circle concentric with the channel 2, with a radius smaller than the radius of the channel 2. It will be appreciated however, that the locations of the write electrodes $5a$ may be swapped with the locations of the read electrodes $5b$ and vice versa. Further, an electrode connection point (formed by an electrode hole 8 and connecting arm 10) may be switched between acting as a connection point for a write electrode $5a$ and a connection point for a read electrode $5b$. Also the outer ring of electrodes could be made up of a mixture of read and write electrodes, as could the inner—for instance, they could alternate in function along the channel (this is also true for straight channel designs).

Similarly to the device 1 described above, the analytes of interest may be injected into the circular channel 2 shown in FIG. 13 as a plug or otherwise through one of the inlets 9 (which can also serve as outlets) arranged in a typical cross injection system. Alternatively, analytes of interest can be pre-mixed with a separation buffer or gel as the initial physical size of the sample is irrelevant, making the cross injection system 9 shown in FIG. 13 optional.

Figure 14:
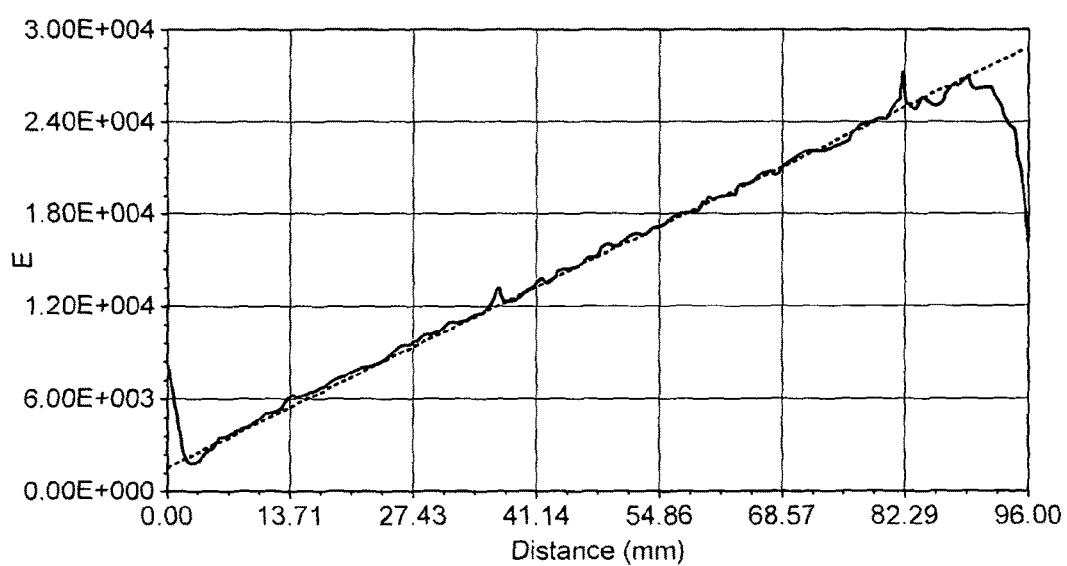
FIG. 14 is a graph illustrating an exemplary electric field profile along a circular channel.

As illustrated in FIG. 14, field edge effects of the sort described above do not occur in a closed loop system such as the circular device of FIG. 13. In this case, the field distortion at the 'edges' is far smaller compared to the distortions shown in FIG. 12 for a linear channel 2. (An 'edge' in the case of a closed loop channel means the boundary of the useful electric field where the field 'reverses' (i.e. travels in the opposite direction) to complete the loop—this is described in WO2006/07176. This is because the electric field is applied around the full loop of the device and hence there is no asymmetric field averaging.

Furthermore, in field shifting systems such as that described in WO2006/070176, the propagating EM wave travels around the loop. This sweeps ions in the electrical interface material 3 around the loop, continuously replenishing any ion denuded regions of the material, so that the field in the channel 2 remains smooth and stable. A further advantage of closed loop systems is that there is no beginning or end to the channel 2 and so the device has essentially an infinite operational length. Apart from exclusively linear or exclusively closed loop channels, it will be appreciated that any combination of linear or curved sections of a channel 2 can be utilised in devices in accordance with the present invention.

Figure 15:
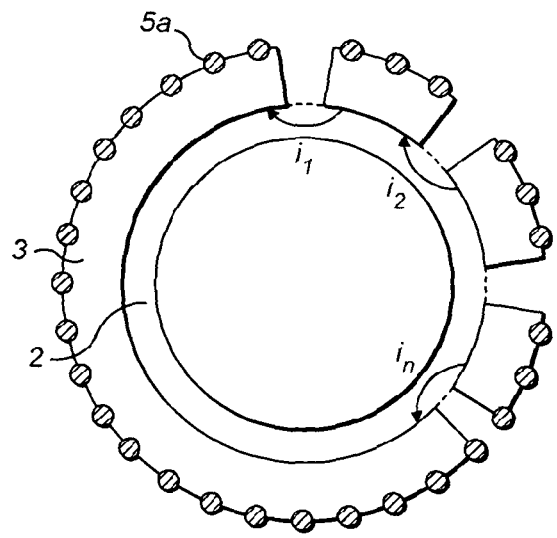
FIG. 15 is a schematic representation of a device having a circular channel and discontinuous interface region.

FIG. 15 is a further schematic representation of another closed loop design, wherein the electrical interface material 3 is interrupted and does not form a continuous region around the channel 2. Even though the electrical interface material 3 is interrupted, electrical connection path $i_1, i_2, \ldots i_n$ forms along the channel 2 and the electrical interface material 3 would still act as a 'closed loop' of material, performing the required smoothing function on the applied electric field. It will be noted that in this embodiment, the electrical interface material 3 is only provided on one side of the channel 2.

Figure 16:
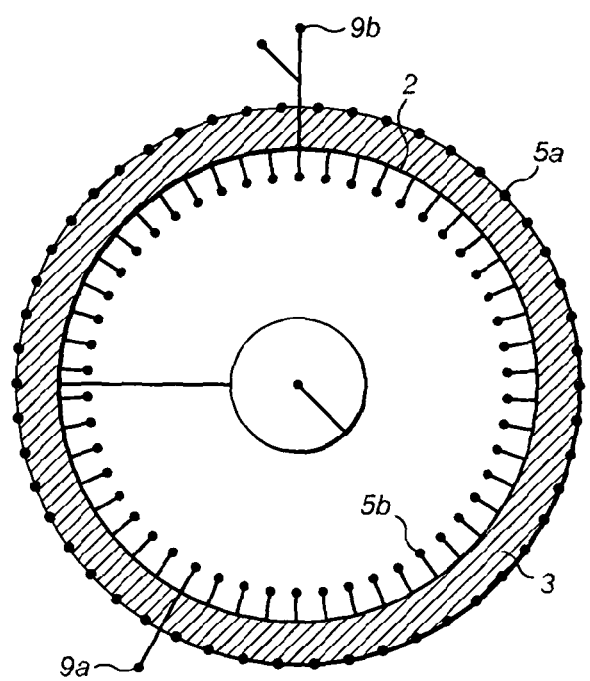
FIG. 16A is a schematic representation of a fourth embodiment, having a circular channel and an asymmetric configuration of electrodes.
FIG. 16B is a schematic representation of a portion of the fourth embodiment, wherein the analytes of interest are separated into 'bands'.

FIG. 16A shows a further closed loop design variant in which the electrical interface material 3 has different widths either side of the channel 2, and the read and write electrodes $5a$, $5b$ are offset with respect to the channel 2 rather than directly opposite one another. The device of FIG. 16A also has a different arrangement of inlets and outlets, 9a and 9b. The electrical interface material 3 is only required on the side of the write electrodes 5a, and voltages can be read by means of nano or micro-channels directly connected to the channel 2. Alternatively, the write electrodes 5a can also be located on the inner circle and read electrodes 5b on the outer circle with respect to the channel 2, or they can alternate in any pattern. The interface material 3 may be positioned accordingly so that it is disposed (only) between the write electrodes and the channel, or could be arranged on both sides of the channel to accommodate a variety of electrode arrangements. In another alternate design, the electric field may also be read by switching the write electrode array 5a to a read array for a short period of time, typically a few milliseconds, by means of the controller 6.

Figure 16B:
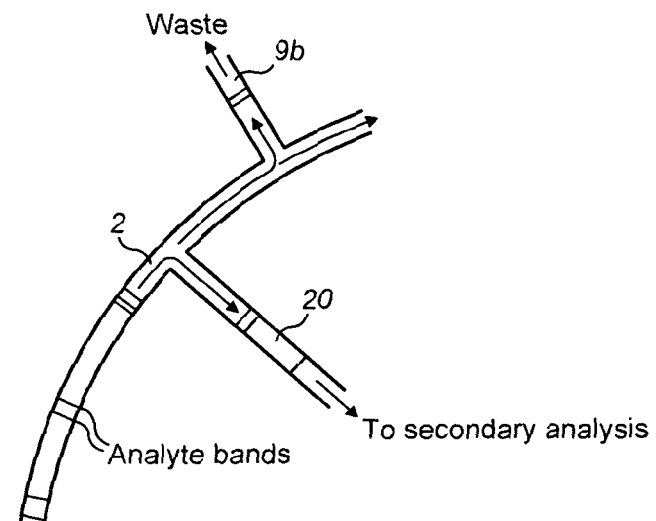

In this example, port 9a acts as an input for the sample while port 9b acts as an output for waste. This is illustrated more clearly in the enlargement of FIG. 16B. Once the objects have been separated into analyte bands A, selected bands can be removed from the analysis through output 9b by activating a suitable electric field within port 9b to attract the band in question and remove it from the main channel 2. Bands removed in this way could be directed to an array of wells for storage, so that each well would contain one analyte, or a range of analytes with very similar mass to charge ratios (q/m). Such wells of arrays could form the basis of a MALDI type plate (the wells would contain a matrix material and be dried before laser desorption), or they could be extracted for subsequent use or secondary analysis. Similarly, bands may be selected for further use or analysis by moving them on to a secondary channel via a connection port 20. This may take the form of a second electrophoresis channel, possibly with a different q/m range "window", or of a different resolution. Alternatively, a different analysis technique, such as mass spectrometry (for example, electrospray ionisation), may be employed. In another example, a 'cascade' of two or more devices could be used, with further analysis of the selected bands taking place in a second (and possibly subsequent) field shifting electrophoresis device arranged to receive samples output from the first device. If desired different field shifting parameters can be selected for each device in order to resolve specific components with a given narrow mobility range for example. In a fully integrated device, the analytes may be fed directly into another section of the chip for use in a biochemical process, for example the DNA may be subject to amplification and/or modification and injected into a cell, or a protein may be introduced to a cell for the evaluation of its effects.

Figure 17A:
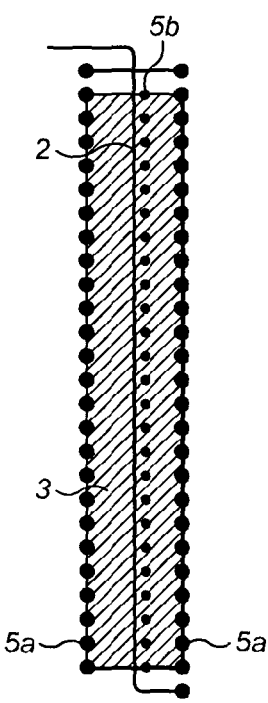
FIGS. 17A and 17B are schematic representations of further embodiments, having linear and circular channels, respectively, and alternative configurations of electrodes and read electrodes located in between write electrodes.
Figure 17B:
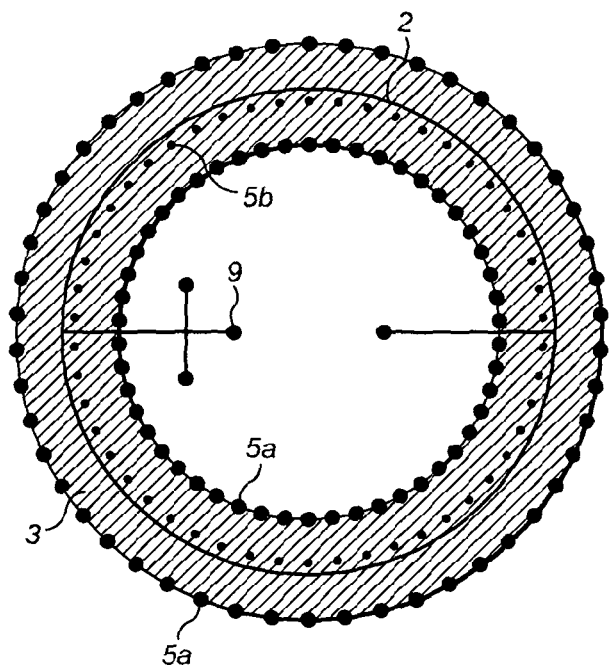

FIGS. 17A and 17B respectively show alternative "symmetrical" designs for linear and closed loop systems. Each design consists of two sets of write electrodes 5a on either side of the channel 2, with a row of read electrodes 5b at one side of the channel. In this example, the electrodes 5a, 5b are connected directly to the electrical interface material 3, i.e. no connecting arms are used. The read electrodes 5b may in fact directly contact the channel 2 itself (i.e. not via the material 3).

Figure 18:
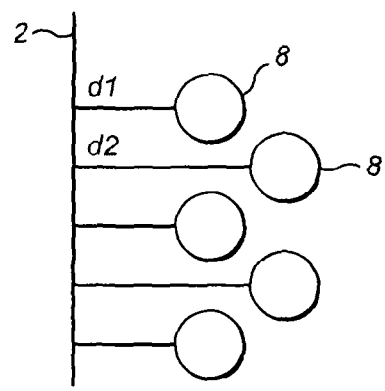
FIG. 18 schematically represents an exemplary staggered configuration of electrodes.

In the embodiments described so far, the connection points at which the electrodes apply or read voltages have been distributed in rows along appropriate lines at a constant spacing from the channel. However, as alluded to above this is not essential and if necessary, fluidic arms may be employed as part of the electric field applying assembly to increase the system's flexibility. In one example, the connection points (holes 8) receiving electrodes may be staggered with respect to the channel 2 as is schematically shown in FIG. 18. This configuration helps maximise space for the holes 8 along the channel meaning that the spacing of the point voltages along the channel can be decreased. This in turn means that the initial discrete electric field is smoother than might otherwise be the case, reducing the amount of further field smoothing required of the material 3 and hence permitting a reduction in its width. In this exemplary pattern, the connection points may alternate between different distances d1, d2 from the channel 2, in order to present the same level of electrical resistance to each electrode.

Figure 19A:
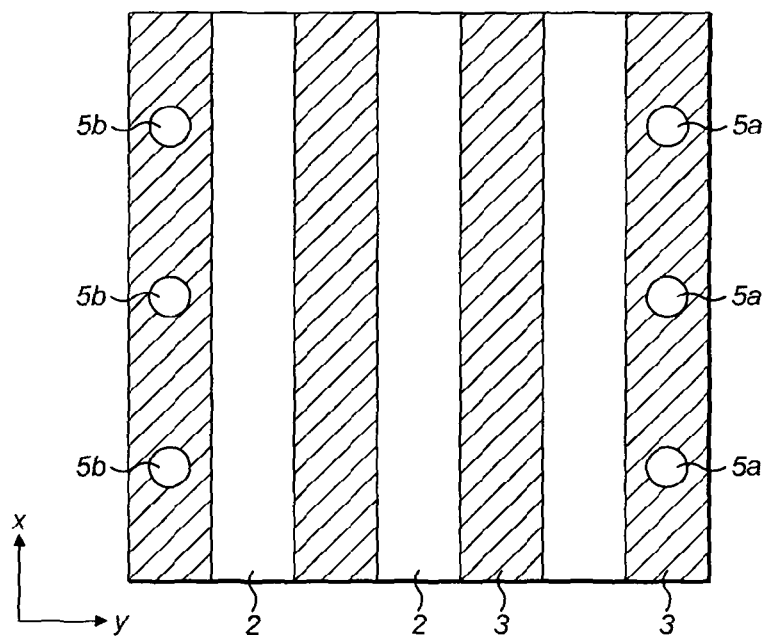
FIGS. 19A and 19B, respectively, show top and cross-sectional views of another embodiment of a portion of a device in accordance with the present invention.
Figure 19B:
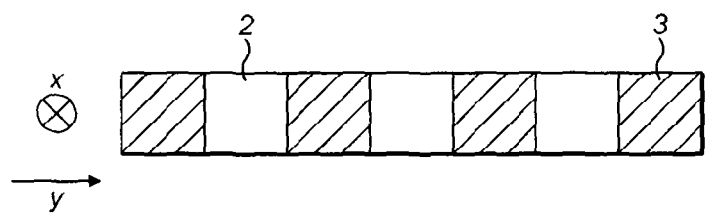

FIGS. 19A and 19B schematically represent top and frontal views, respectively of a further chip configuration which comprises a plurality of channels 2. The channels 2 are linear and typically arranged in parallel and spaced from each other by electrical interface material 3. Another typical configuration would comprise several concentric closed-loop channels 2. It will be appreciated however that any combination of multiple linear or curved channels 2 is possible. Each channel 2 could be provided with connection points (holes 8) for receiving electrodes in order to apply an electric field separately to each channel 2. However, as shown in FIG. 18, it is preferred that a single set of connection points for write electrodes and optionally read electrodes are provided. The electrical interface material is arranged between each of the channels such that it presents a smoothed version of the applied electric field to each channel. Preferably the field established in each channel will be substantially the same and this will typically be the case where the conductivity/resistivity of the electrical interface material is homogenous in all regions.

However, if it is desired to establish electric fields of different strengths in each channel, this can be achieved by varying the conductivity/resistivity of the electrical interface material, for example, in the y direction (across the channels). Application of a discrete electric field by one electric field applying assembly would then give rise to a smoothed electric field of the desired magnitude in each channel. As described above, variation in the material's conductivity/resistivity can be achieved through engineering of the material itself or by the inclusion of features such as pillars in the cavity or variation in cavity depth (thickness).

If the conductivity/resistivity of the electrical interface material varies only in the direction across the channels, the electric field established within each channel will be of a similar shape. However, if the conductivity/resistivity is varied (additionally or alternatively) in the direction along the channels (here, the x-direction), different field profile shapes can be achieved in each channel from the same applied discrete electric field.

Devices including multiple channels 2 may be manufactured by the same techniques described above. In particular, the photo-patterning of liquid polymers to form the electrical interface material 3 is particularly suitable for these devices. However, it has also been found that, if the dimensions of an internal cavity are selected appropriately, filling by capillary action can also achieve the desired result, with the liquid interface material 3 filling each cavity region whilst leaving the channels 2 substantially empty.

As discussed above, it will be appreciated that the devices and methods in accordance with the exemplary embodiments described herein have widespread applications, and may be used in any device having a conducting volume which requires the application of a smooth electric field. The techniques are particularly useful wherever a shaped (non-uniform) electric field is desired. The exemplary embodiments described above have focused on electrophoresis applications for separating objects in separation channels 2, but it will be understood that this is not intended to be limiting.

In alternative embodiments, the conducting volume may be, for example a hydrophilic paper region made on a hydrophobic paper substrate. The electrical interface material 3 may be provided along the sides of the hydrophilic region and the write electrodes may, for example, be screen printed onto the paper such that they overlap with the electric field interface material 3, but not with the hydrophilic region. The electrical interface material 3 could be for example, spin coated, moulded or simply poured on the paper and photo-patterned as required. Objects to be separated may then be introduced into the hydrophilic paper region to be separated upon application of the electric field.

In other examples, the conducting volume 2 may take the form of any volume in which fluids and/or objects of interest can be accommodated (and/or may move through) during analysis. The conducting volume 2 need not itself physically constrain the path of the fluid and/or analyte, for example in a 'free flow' electrophoresis device. 'Free flow' electrophoresis devices typically involve an electrolyte being pumped through a chamber so that there is a hydrodynamic flow through the device. Analytes of interest are pumped in with the electrolyte. Strip electrodes may be placed along the chamber, aligned with the direction of the flow and spaced in a perpendicular direction. The electric field may be shifted perpendicular to the direction of flow, so that the analytes focus into separate streams which can be isolated at the bottom of the device into different channels.

Figure 20A:
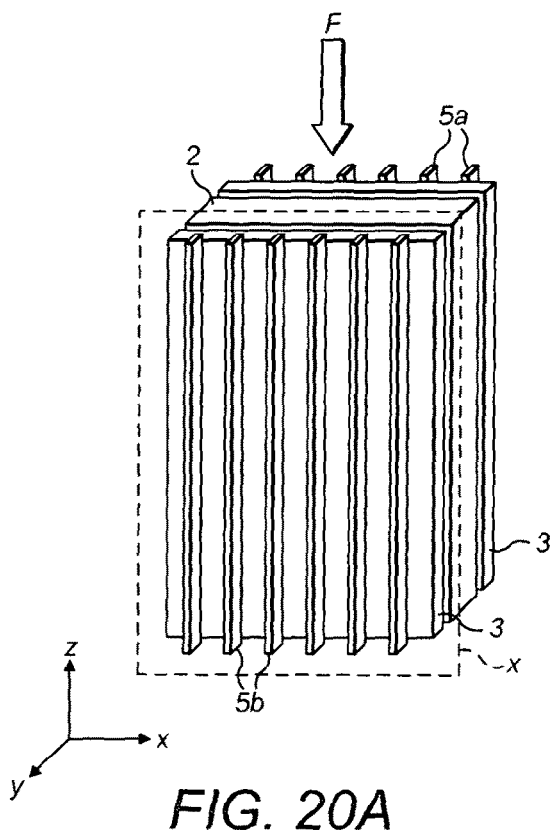
FIGS. 20A, 20B, 21, and 22 illustrate further embodiments of devices.
Figure 20B:
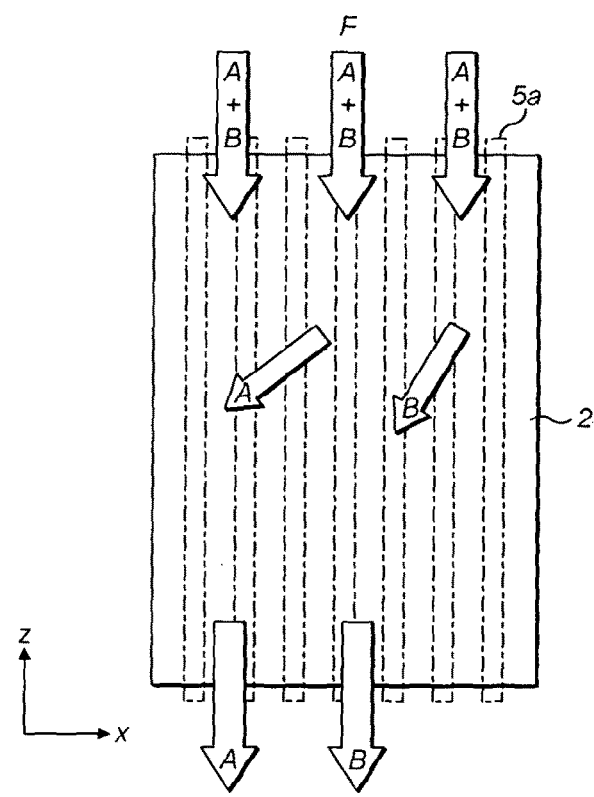

An example of a 'free flow' electrophoresis device in accordance with the present invention is depicted in FIGS. 20*a* and 20*b*. Elongated write electrodes 5*a* may be formed on a porous hydrophobic substrate (not illustrated). The porous hydrophobic layer is provided to allow gas from electrolysis to escape, however it is not essential.

The electrodes 5*a* may be oriented vertically, dipped in vertically oriented wells so that the fluid or buffer is retained in the wells. Advantageously, gas bubbles resulting from electrolysis can move upwards and leave the well. A layer of electrical interface material 3 may then be deposited on top of the electrodes and then patterned with an array of pillars (not shown). Another layer of electrical interface material 3 may be added on top and the conducting volume 2 is formed as a patterned cavity between the two layers of electrical interface material 3 which are spaced by the pillars. On top of the upper electrical interface material layer 3, more vertical electrodes may be provided as read electrodes 5*b*.

Objects to be separated may then be introduced in the conducting volume 2 at the top of the device and continuously pumped through the cavity as illustrated by arrow F. The electric field may be shifted from one side of the cavity to the other, perpendicular to the flow F, leading to highly focused separation of the objects moving inside the cavity along separate paths. As illustrated in the cross section of FIG. 20(*b*), the sample may initially include objects of two different types, A and B. Each will undergo a different lateral motion due to the applied field as depicted schematically by the arrows marked A and B, The separated objects may be collected in separate channels provided at the bottom of the conducting volume 2. Advantageously, even in cases when the conducting volume 2 is not a closed loop, such devices can operate continuously, being very useful for the separation of large quantities of samples, e.g. for preparative chemistry.

Alternatively, the electrodes 5*a* may be oriented horizontally. In this configuration, instead of providing horizontal wells on the 'side' of the device (which would have the undesired effect of letting the fluid in the wells flow out), there is provided a channel-like 'long well' filled with buffer and having several small holes along the channel which act as exhausts for the gas bubbles.

In another example, the conductive volume may comprise a "slab-gel", which is a commonly used term for a substantially planar region of sieving matrix, formed on the surface of a slide or chip for example. Components of this sort are typically used in DNA and protein analysis.

Figure 21:
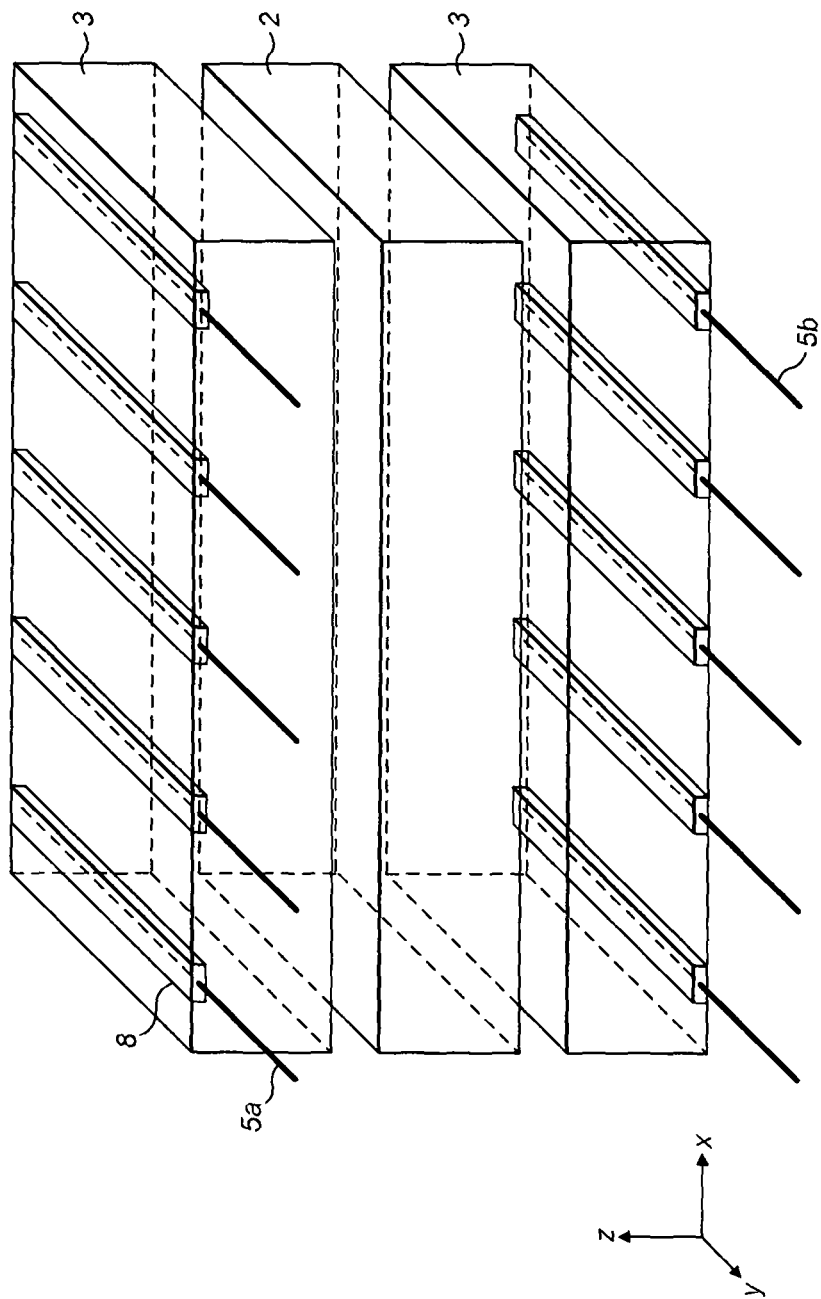

An embodiment in which the above principles are applied to a slab-gel type arrangement is shown in FIG. 21. Here, parallel linear read electrodes 5*b* are placed in contact with a first region of electrical interface material 5*b* on top of which a layer of separation gel 2 is deposited in a slab gel type format. The electrodes may be oriented vertically, or horizontally, dipped in 'long wells' as described above. A second region of electrical interface material 3 is deposited on top of the slab gel 2 and another set of parallel linear electrodes are placed in contact with the upper electrical interface material 3 to form the write electrodes 5*a*. Of course, the function of each set of electrodes could be swapped such that the lower set serves as a field generator, and the upper set as field measuring electrodes.

In use, a sample containing analyte(s) is introduced to the slab gel at one end of the system and the electric field is applied as required to focus and separate the sample into its constituent components. The sample moves perpendicularly to the linear electrodes during the separation process (in the x direction).

Figure 22:
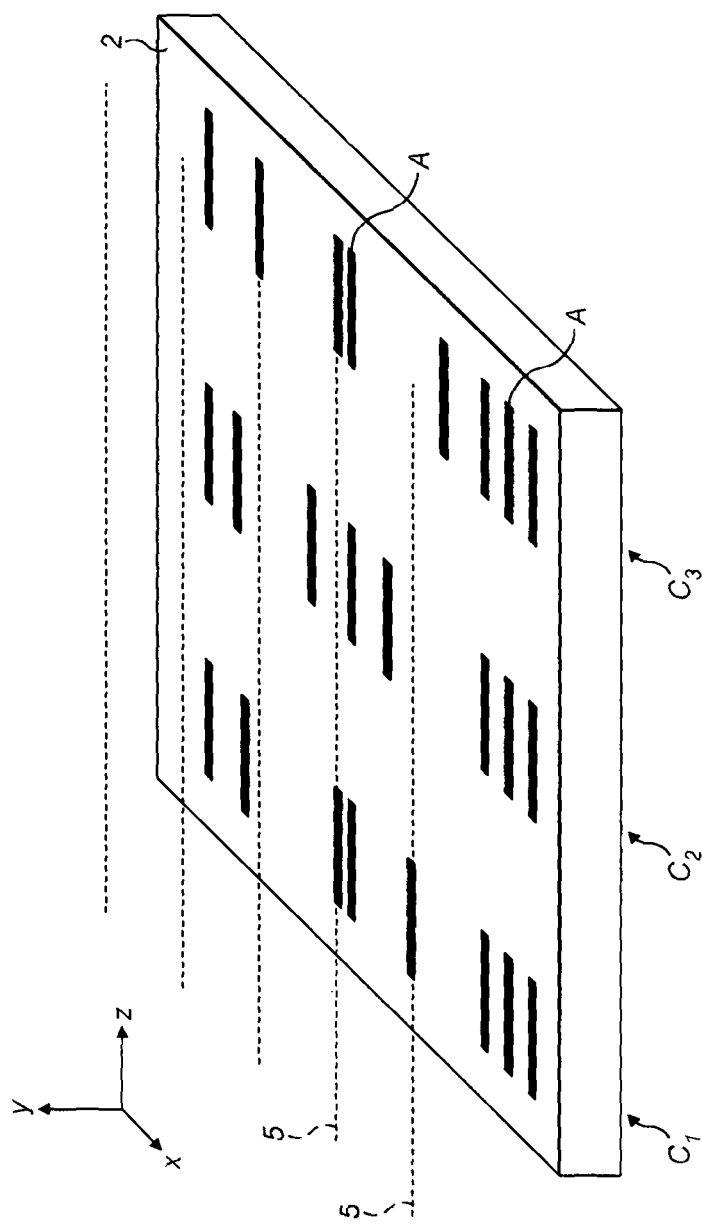

For clarity, FIG. 22 illustrates the slab-gel 2 with the other device components removed so that the results of separation can be seen. Note the slab-gel is depicted in a different orientation to that shown in FIG. 21. Here, the positions of the linear electrodes are indicated by the dashed lines marked 5. The analyte has separated into bands A along three separate "channels" $C_1$, $C_2$, $C_3$ according to the starting position of the three samples applied to the slab-gel. There is no need for a physical barrier between each of the virtual "channels", although this could be included if desired.

What is claimed is:

1. A device comprising:
   an electric field applying assembly adapted to generate an electric field having a discrete electric field profile, wherein the electric field applying assembly comprises a plurality of electrodes in electrical contact with the electrical interface region;
   a conducting volume; and
   an electrical interface region, provided between the conducting volume and the electric field applying assembly, the electrical interface region arranged such that the discrete electric field is applied to the electrical interface region by the electric field applying assembly at a location spaced from the conducting volume;
   wherein the electrical interface region comprises at least an ionically conductive material arranged adjacent to and in contact with the conducting volume;
   such that the discrete electric field applied by the electric field applying assembly is smoothed by the electrical interface region so that the electric field profile established within the conducting volume is substantially continuous.

2. A device according to claim 1, wherein the distance between the location at which the electric field is applied and the conducting volume is at least the thickness of the electrical interface region in a direction perpendicular to both said distance and the conducting volume, preferably at least twice, more preferably at least 5 times, still more preferably at least 10 times, most preferably at least 100 times.

3. A device according to claim 1, wherein the electric interface region substantially fills a cavity provided in a substrate.

4. A device according to claim 3, wherein the cavity is provided with at least one pillar extending between opposing walls of the cavity.

5. A device according to claim 1, wherein the height of the conducting volume is approximately equal to or greater than the thickness of the interface region in the same direction.

6. A device according to claim 5, wherein the height of the conducting volume is between 1 and 5 times greater than the thickness of the interface region in the same direction, preferably between 1 and 3 times greater, still preferably around 2 times greater.

7. A device according to claim 5, wherein the substrate is provided with at least one well in connection with the cavity and with a surface of the substrate, for accommodating an electrode in use.

8. A device according to claim 7, wherein the at least one well is fluidly connected to the cavity via a connection arm of the electric field applying assembly adapted to contain a conductive fluid in use.

9. A device according to claim 7, comprising a plurality of wells spaced along a direction conforming to the periphery of the conducting volume.

10. A device according to claim 7, further comprising:
 a first plurality of wells provided along a direction conforming to the periphery of the conducting volume, wherein each well in the first plurality of wells is located at a first distance from the conducting volume, and
 a second plurality of wells provided along a direction conforming to the path of the conducting volume, wherein each well in the second plurality of wells is located at a second distance from the conducting volume,
 such that the wells in the first plurality of wells are staggered with respect to the wells in the second plurality of wells in a direction perpendicular to the periphery of the conducting volume.

11. A device according to claim 1, wherein the conducting volume is a channel.

12. A device according to claim 1, wherein the electrodes are spaced along a direction conforming to the periphery of the conducting volume.

13. A device according to claim 1, wherein the plurality of electrodes is arranged along one side of the conducting volume.

14. A device according to claim 1, wherein the electric field applying assembly further comprises a second plurality of electrodes arranged along the opposite side of the conducting volume from the first plurality of electrodes, thereby forming pairs of electrodes on opposite sides of the conducting volume.

15. A device according to claim 1, wherein the device further comprises an electric field measuring assembly adapted to measure the electric field within the conducting volume and wherein the controller is adapted to vary the applied discrete electric field based on the measured electric field.

16. A device according to claim 15, wherein the electric field measuring assembly comprises a plurality of electrodes in electrical contact with the electrical interface region, the plurality of electrodes of the electric field measuring assembly preferably being arranged on the opposite side of the conducting volume from the electric field applying assembly.

17. A device according to claim 15, wherein the electric field measuring assembly comprises a plurality of electrodes in direct contact with the conducting volume.

18. A device according to claim 1, wherein the electrical interface region consists of the ionically conductive material.

19. A device according to claim 1, wherein the electrical interface region comprises the ionically conductive material and a non-ionically conductive material, such that the ionically conductive material is located between the non-ionically conductive material and the conducting volume and the discrete electric field is applied by the electric field applying assembly to the non-ionically conductive material.

20. A device according to claim 19, wherein the conductivity of the non-ionically conductive material and the conductivity of the ionically conductive material are matched such that both the non-ionically conductive material and the ionically conductive material contribute to the smoothing of the discrete electric field.

21. A device according to claim 1, wherein the ionically conductive material is electrically insulating.

22. A device according to claim 1, wherein the ionically conductive material is one of: a polymer; a porous material, such that fluid can pass through the material; a hydrogel; a porous glass or a porous ceramic material.

23. A device according to claim 1, wherein the conducting volume is filled with an ionic conductor which has a conductivity of the same order to the conductivity of the ionically conductive material, and preferably equal to the conductivity of the ionically conductive material.

24. A device according to claim 1, wherein the resistivity of the electric field interface region is variable in one direction.

25. A device according to claim 1, wherein the conducting volume comprises a plurality of channels, each channel being laterally spaced from the next by a portion of electrical interface region, wherein the electric field applying assembly is configured to apply the discrete electric field to one portion of the electrical interface region, whereby the discrete electric field is smoothed by the electrical interface region such that a substantially continuous electric field is established in each of the channels.

26. A device according to claim 25, wherein the substantially continuous electric field established in each channel is substantially the same.

27. A device according to claim 1, wherein the device is a device for separating objects and wherein the conducting volume is a separation channel which, in use, contains objects to be separated, whereby the substantially continuous electric field in the channel gives rise to an electric force acting on each object; and the device further comprises:
 a balancing source configured to give rise to a force opposing the electric force on each object;
 whereby objects in the separation channel are caused cause to separate into bands under the combined influence of the electric field and the balancing source.

28. An electrophoresis device for separating objects according to claim 27, wherein the balancing source is a fluid contained in the separation channel together with the objects to be separated, the device further comprising a controller adapted to vary the applied discrete electric field so as to adjust the electric field profile relative to the separation channel, whereby objects in the separation channel are caused to separate into bands under the combined influences of an electric force due to the electric field established within the channel and a hydrodynamic force due to the fluid.

* * * * *